US012744986B2

(12) United States Patent
Fernandez-Dorado et al.

(10) Patent No.: US 12,744,986 B2
(45) Date of Patent: Sep. 22, 2026

(54) MACHINE VISION SYSTEM AND METHOD WITH MULTISPECTRAL LIGHT ASSEMBLY

(71) Applicant: COGNEX CORPORATION, Natick, MA (US)

(72) Inventors: Jose Fernandez-Dorado, Vaals (NL); Laurens Nunnink, Simpelveld (NL)

(73) Assignee: Cognex Corporation, Natick, MA (US)

( * ) Notice: Subject to any disclaimer, the term of this patent is extended or adjusted under 35 U.S.C. 154(b) by 697 days.

(21) Appl. No.: 17/568,417

(22) Filed: Jan. 4, 2022

(65) Prior Publication Data

US 2023/0030276 A1 Feb. 2, 2023

Related U.S. Application Data

(63) Continuation-in-part of application No. 17/390,920, filed on Jul. 31, 2021, now Pat. No. 11,717,973.

(51) Int. Cl.
*H04N 23/00* (2023.01)
*A61B 1/06* (2006.01)
(Continued)

(52) U.S. Cl.
CPC ............... *H04N 23/56* (2023.01); *A61B 1/06* (2013.01); *G01J 1/44* (2013.01); *G01S 17/36* (2013.01);
(Continued)

(58) Field of Classification Search
CPC ........ H04N 23/56; H04N 23/51; H04N 23/55; H04N 23/71; A61B 1/06; A61B 1/0607;
(Continued)

(56) References Cited

U.S. PATENT DOCUMENTS 5,914,481 A 6/1999 Danielson et al.
8,456,107 B2 * 6/2013 Salm ................. G03B 21/2033 315/307

(Continued)

FOREIGN PATENT DOCUMENTS

CN 103714307 A 4/2014
EP 1771766 A1 4/2007

(Continued)

OTHER PUBLICATIONS

PCT/US2022/038842—International Search Report and Written Opinion—Feb. 21, 2023, 32 pages.

(Continued)

*Primary Examiner* — Henry Duong
(74) *Attorney, Agent, or Firm* — Quarles & Brady LLP

(57) ABSTRACT

A machine vision system can include an image sensor assembly including an image sensor, a lens assembly coupled to the image sensor assembly, an illumination assembly coupled to the lens assembly, and a removable front cover positioned in front of the illumination assembly. The illumination assembly can include a plurality of multi-spectral light assemblies. Each multispectral light assembly of the plurality of multispectral light assemblies can include a multispectral light source having a plurality of color LED dies configured to generate at least two different wave-lengths of light, a light pipe positioned in front of the multispectral light source and having an exit surface, a diffusive surface on the exit surface of the light pipe, and a projection lens positioned in front of the diffusive surface. The machine vision system can also include an illumination sensor configured to detect light from the illumination assembly.

19 Claims, 17 Drawing Sheets

(51) Int. Cl.

| | |
|---|---|
| ***G01J 1/44*** | (2006.01) |
| ***G01S 17/36*** | (2006.01) |
| ***G02B 1/04*** | (2006.01) |
| ***H04N 23/51*** | (2023.01) |
| ***H04N 23/55*** | (2023.01) |
| ***H04N 23/56*** | (2023.01) |
| ***H04N 23/71*** | (2023.01) |

(52) U.S. Cl.
CPC ............. *G02B 1/041* (2013.01); *H04N 23/51* (2023.01); *H04N 23/55* (2023.01); *H04N 23/71* (2023.01); *G01J 2001/446* (2013.01)

(58) Field of Classification Search
CPC ..... A61B 1/0615; A61B 1/0623; A61B 1/063; A61B 1/0638; A61B 1/0653; A61B 1/0661; A61B 1/0676; A61B 1/0669; A61B 1/0684; G01J 1/44; G01J 2001/446; G01S 17/36; G02B 1/041; G02B 7/02; G02B 7/08; G02B 25/002; G02B 25/004; G02B 25/005; G02B 25/008; G02B 25/007; G02B 25/02; G06K 7/10742; G06K 7/10752; G06K 7/10811; G06K 7/10831; G06K 7/12; G06K 7/14; G06K 7/10732; F21V 5/00; F21V 5/008; F21V 5/04; F21V 5/041; F21V 5/043; F21V 5/045; F21V 5/046; F21V 5/048; F21V 5/10
USPC .......................................................... 359/800
See application file for complete search history.

(56) References Cited

U.S. PATENT DOCUMENTS

| | | | | |
|---|---|---|---|---|
| 8,704,944 | B1 * | 4/2014 | Wierzoch | H04N 23/66 348/207.99 |
| 9,576,169 | B2 | 2/2017 | Wang et al. | |
| 10,168,216 | B2 | 1/2019 | Kido | |
| 2006/0202038 | A1 | 9/2006 | Wang et al. | |
| 2011/0080729 | A1 | 4/2011 | Nunnink et al. | |
| 2013/0292477 | A1 | 11/2013 | Hennick et al. | |
| 2014/0183264 | A1 * | 7/2014 | Nunnink | G06K 7/10831 235/462.24 |
| 2014/0203086 | A1 | 7/2014 | Wang et al. | |
| 2016/0110574 | A1 | 4/2016 | Wang et al. | |
| 2017/0167919 | A1 | 6/2017 | Learmonth et al. | |
| 2018/0328855 | A1 | 11/2018 | Kido | |
| 2018/0330489 | A1 | 11/2018 | Kido | |
| 2018/0330490 | A1 | 11/2018 | Kido | |
| 2019/0141261 | A1 | 5/2019 | Hogasten et al. | |
| 2021/0334488 | A1 | 10/2021 | Feng et al. | |
| 2022/0125280 | A1 * | 4/2022 | Tyan | A61B 5/0035 |
| 2023/0358891 | A1 * | 11/2023 | Carr | G01S 17/42 |

FOREIGN PATENT DOCUMENTS

| | | | |
|---|---|---|---|
| EP | 2372765 | A1 | 10/2011 |
| EP | 3005221 | A1 | 4/2016 |
| EP | 3401845 | A1 | 11/2018 |
| EP | 3647989 | A1 | 5/2020 |
| EP | 3559855 | B1 | 11/2021 |
| JP | 2006-313147 | A | 11/2006 |
| JP | 2019-521331 | A | 7/2019 |
| JP | 2021-018086 | A | 2/2021 |
| WO | 2018209580 | A1 | 11/2018 |

OTHER PUBLICATIONS

Code Corporation, Code Reader 6000, https://codecorp.com/products/code-reader-6000, Copyright 2020, 1 page.
Datalogic, Products, https://www.datalogic.com/eng/powerscan-pbt9500-dpm-evo-hp-624.html, Copyright 2022, 1 page.
Keyence Corporation, Autofocus 1D and 2D Code Reader, https://www.keyence.com/products/barcode/barcode-readers/sr-1000, Copyright 2021, 3 pages.
Keyence Corporation, Handheld DPM Code Reader, https://www.keyence.ca/products/barcode/handheld-scanner/sr-g100/?ad_local=sitetopslbn2, Copyright 2021, 2 pages.
Keyence Corporation, Multi-Spectral Lighting (50 mm), https://www.keyence.com/products/vision/vision-sys/ca-d/models/ca-drm5x/, 2022, 2 pages.
Keyence Corporation, Multi Spectrum Vision System, https://www.keyence.com/landing/lpc/multispectrum_cvx42.jsp, 2022, 2 pages.
Ledil, Product Datasheet, CP10960_RGBX-SS (Spot Beam), Published: Sep. 25, 2018, Last Update: Feb. 7, 2022, 5 pages.
Opt Machine Vision, Ring Lights OPT-RI Series, https://en.optmv.com/content/details16_190.html, Printed Feb. 9, 2022, 2 pages.
Opt Machine Vision, Dome Lights OPT-RID Series, https://en.optmv.com/content/details16_766.html, Printed Feb. 9, 2022, 2 pages.
Panasonic Corporation, Laser Markers / 2D Code Readers, https://www3.panasonic.biz/ac/e/fasys/lasermarker/index, Printed Dec. 13, 2021, 2 pages.
Sun et al., Collimating Lamp with Well Color Mixing of Red/Green/Blue LEDs, Optics Express, 2012, 20(S1):A75-A84.
Office Action for JP 2024-506216, dated Apr. 22, 2025, 9 pages.

* cited by examiner 1102
1120
1114
1118
1116
1128
1112
1124
1122
1104
1106
1126
1122
1122
1100
1108
1110

1152
1130
1106
1152
1150

MACHINE VISION SYSTEM AND METHOD WITH MULTISPECTRAL LIGHT ASSEMBLY

CROSS-REFERENCE TO RELATED APPLICATIONS

This application is a continuation-in-part of co-pending U.S. patent application Ser. No. 17/390,920, filed on Jul. 31, 2021, entitled "Machine Vision System and Method with Multispectral Light Assembly," which is incorporated herein by reference in its entirety.

FIELD

The present disclosure relates generally to machine vision systems and, more particularly, to an illumination system with a plurality of multispectral light assemblies and a method for controlling the multispectral light assemblies.

BACKGROUND

Machine vision systems (also simply termed "vision systems") use image acquisition devices that include image sensors to deliver information on a viewed subject. The system can then interpret this information according to a variety of algorithms to perform programmed decision-making or identification functions. For example, an image of an object containing features of interest to the system can be acquired by an on-board image sensor (also referred to as simply an "imager" or "sensor") in the visible or near visible light range under appropriate illumination, which can be based upon ambient light or light provided by an internal or external illuminator.

Vision systems may be used for a variety of tasks in manufacturing, logistics and industry. A common task for vision systems is the reading and decoding of symbology (e.g., one-dimensional and two-dimensional codes—also termed "IDs"), which are used in a wide variety of applications and industries and can take the form of ID barcodes, 2D DataMatrix Codes, QR Codes and Dot-Codes, among other. The image sensor acquires images (typically grayscale or color, and in one, two, or three dimensions) of the subject or object, and processes these acquired images using an on-board or interconnected vision system processor. The processor often includes both processing hardware and non-transitory computer-readable program instructions (software) that perform one or more vision system processes to generate a desired output based upon the image's processed information. This image information is typically provided within an array of image pixels each having various colors or intensities. In the example of an ID reader (also termed herein, a "reader"), the user or an automated process acquires an image of an object that is believed to contain one or more barcodes, 2D codes or other ID types. The image is processed to identify encoded features, which are then decoded by a decoding process or processes to obtain the inherent alphanumeric data represented by the code.

Vision systems may also be used for other tasks such as, for example, surface and parts inspection, alignment of objects during assembly, measurement, and any other operations in which visual data is acquired and interpreted for use in further processes. For example, a vision system may be used to inspect objects (e.g., components or parts) on a production line (e.g., during manufacturing processes) to ensure that the objects meet predefined criteria. For example, each object may be expected to contain certain features or characteristics. In an inspection process, the image sensor of the vision system may acquire images of an object and the images may be processed (e.g., using a vision system processor) to identify features or characteristics of the object. The results of the inspection process may be provided to a display for viewing by an operator. If the object passes the inspection, the object may be kept on the production line for further processing and/or handling. If the object fails the inspection, the object may be marked and/or removed from the production line.

SUMMARY

In accordance with an embodiment, a machine vision system includes an image sensor assembly including an image sensor, a lens assembly coupled to the image sensor assembly, an illumination assembly coupled to the lens assembly, and a removable front cover positioned in front of the illumination assembly. The illumination assembly can include a plurality of multispectral light assemblies. Each multispectral light assembly of the plurality of multispectral light assemblies can include a multispectral light source having a plurality of color LED dies configured to generate at least two different wavelengths of light, a light pipe positioned in front of the multispectral light source and having an exit surface, a diffusive surface on the exit surface of the light pipe, and a projection lens positioned in front of the diffusive surface.

In accordance with another embodiment, a machine vision system includes an image sensor assembly including an image sensor, and a lens assembly coupled to the image sensor assembly. The lens assembly can include a plurality of lenses and a first gear positioned around the lens assembly. The machine vision system can further include an illumination assembly coupled to the lens assembly, and a removable front cover positioned in front of the illumination assembly. The illumination assembly can include a housing, a gear mechanism movably engaged with the first gear on the lens assembly, an outer surface having an opening configured to receive a tool to adjust the focus of the lens assembly, a front plate having a plurality of openings, and a plurality of multispectral light assemblies.

BRIEF DESCRIPTION OF THE DRAWINGS

The present disclosure will hereafter be described with reference to the accompanying drawings, wherein like reference numerals denote like elements.

DETAILED DESCRIPTION

Figure 1:
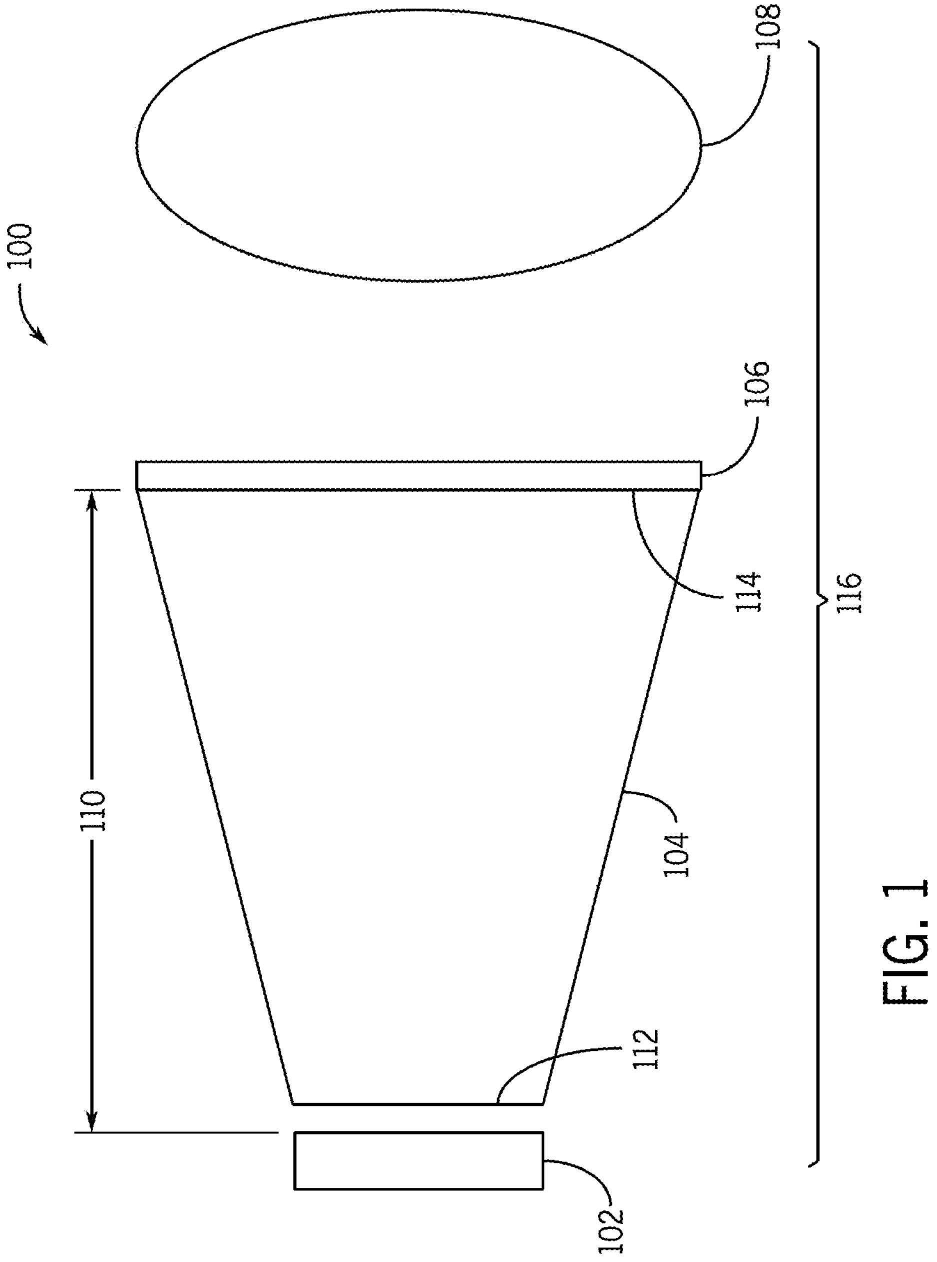
FIG. 1 is a schematic diagram of a multispectral light assembly in accordance with an embodiment of the technology.

Visions systems may be used in a variety of applications including reading and decoding IDs (e.g., barcodes), inspecting objects and surfaces, alignment of objects during assembly, measurement, and any other operations in which visual data is acquired and interpreted for use in further processes. ID (e.g., barcode) readers are generally configured to track and sort objects, including along a line (e.g., a conveyor) in manufacturing and logistics operations. The ID reader, or more typically, a plurality (constellation) of readers can be positioned over the line (or otherwise) at an appropriate viewing angle(s) to acquire any expected ID codes on the face(s) of respective objects as they each move through the field of view. The ID reader can also be provided in a handheld configuration that allows the user to move from object to object, for example, on an inspection floor and vary the distance or relative angle between the reader and object surface at will. More generally, the focus distance of the ID reader with respect to the object can vary, depending on the placement of the reader with respect to the line and the size of the object. Visions systems for inspection are generally configured to capture an image of an object (e.g., a component or part) on a production or assembly line, processing the image to determine if the object meets a predefined criteria (e.g., one or more expected features are present), and report the inspection results. Such machine vision systems may aid in the inspection, assembly, and/or handling of various types of articles, parts, and devices, including automotive parts (e.g., fuses, gaskets, and spark plugs), electrical components (e.g., connector pins, keyboards, LED, LCD displays), medical and pharmaceutical products (e.g., disposable test kits, syringes, needles, and date-lot codes), and consumer products (e.g., razor blades and floppy disks).

In operation, some vision systems (e.g., ID readers or inspection systems) or associated lighting attachments function to illuminate the scene containing one or more objects (e.g., ID's, components or parts). For an ID reader, this illumination can include aimers that project a colored dot on the region of interest in the imaged scene, whereby the user can center the image axis of the reader on the barcode within the imaged scene. Illumination for a vision system can also include general illumination to allow acquisition of appropriately detailed images. The illuminated scene is then acquired by an image sensor within the imaging system through optics. The array of pixels of the sensor is exposed, and the electronic value(s) generated for each pixel by the exposure is/are stored in an array of memory cells, as can be termed the "image" of the scene. In the context of an ID-reading application, the scene can include an object of interest that has one or more IDs of appropriate dimensions and type (e.g., DPM codes, printed barcodes, etc.). The ID(s) are part of the stored image. In the context of an inspection system, the scene can include an area encompassing all pertinent portions of the object of interest in the field of view and the area around the object of interest.

Vision systems may utilize multispectral light sources for illumination of an object for various applications where color (or other multi-wavelength) images are advantageous. As used herein, a multispectral light source is a light source that can separately generate a plurality of different wavelengths of light (e.g., a light source assembly that includes a plurality of distinct light sub-assemblies, each of which can generate a different respective wavelength peak or band. For example, multispectral light sources such as red, green, blue, yellow, infrared (IR), or ultraviolet (UV) light emitting diodes (LEDs) may be used in a vision system to provide multispectral capabilities.

Many conventional systems with multispectral light sources use a diffuser (e.g., a Lambertian diffuser) with the multispectral light source. A diffuser typically may be formed from a sheet of milky white and transparent material that completely diffuses the light in all directions, such that the light projected generally toward an imaging area may be spread out almost 180°. This can result in a more intense core illumination, with the intensity of light dropping off at larger angles. Despite this effect, a diffuser can generally spread out the light over an area with relatively uniform light distribution and can sometimes be used to provide relatively good color mixing uniformity, however, a diffuser increases the physical size and the etendue of the system which can significantly reduce the efficiency. As a result, the working distance of multispectral lights which use a diffuser is usually short (e.g., 0.3 m maximum). The loss of light from a diffuser also makes it difficult to use with different light banks. In addition, conventional systems with multispectral capabilities may require a large number (e.g., 80-100) of monochromatic LED's for each wavelength (i.e., each color). Further, to achieve color uniformity, many conventional systems illuminate using the different LEDs simultaneously with different intensities.

Among other aspects, the present disclosure describes a vision system (and related method) that includes a compact illumination assembly having a plurality of multispectral light assemblies that can be used to project direct light (e.g., color mixed) into a well-defined and relatively uniformly illuminated area. For example, each multispectral light assembly of a plurality of light assemblies can include a multispectral light source with a plurality of LEDs with different wavelengths, and a light pipe. In some embodiments, a multispectral light assembly can further include one or more of a diffusive surface or a projection lens. In an embodiment, the multispectral light source includes various color LED dies in a single package which can reduce the number of LEDs in the illumination system. For example, in some embodiments the multispectral light source may be a RGB LED, an RGBW LED, a RGB(IR) LED, an RGBY LED, an IR and Red LED, a White and Red LED or other RGB or multi-wavelength LED type.

Advantageously, in some embodiments, a light pipe in a multispectral light assembly can enable color mixing of a plurality of colors, homogenize the different spectrums, and correct for non-uniformity caused by off-axis placement of the different color dies in the multispectral light source. As a further advantage, the multispectral light assemblies can generally generate more direct light (rather than diffuse) at longer distances. For example, in an embodiment, the disclosed multispectral light assembly may be used in a vision system to acquire images of an object at up to 1.0 m working distance. In some embodiments, the light from the multispectral light assembly may be projected efficiently in a rectangular area that has a shape that is approximately equal to the field of view (FOV) of the camera of the vision system (e.g., is rectangular for a rectangular FOV, with or without rounded, chamfered, or otherwise truncated corners, and with an aspect ratio that is within 5%, 10%, or 20% of the aspect ratio of the FOV). In some embodiments, the light from the multispectral light assembly may be projected in areas with other shapes such as a square. Advantageously, a vision system incorporating one or more of the multispectral light assemblies may provide direct color mixed light using the one or more multispectral light assemblies allowing for an extended working range with the minimum number of multispectral light sources.

In another aspect, the present disclosure describes an optimized orientation of the LED dies in the multispectral light assemblies to provide balance and symmetry between quadrants of the light projected by the illumination system, for example, to provide similar intensity at the center and the edges of the illumination area. The optimized orientation can also be designed based on desired size and space constraints for the vision system. A further advantage of the disclosed system is that the multispectral light assemblies in the illumination assembly may be positioned in banks symmetrically around the lens of the vision system. Advantageously, this can enable the system to be used for vision system applications that require directed light from different directions. In some embodiments, the improved LED orientation or the improved bank arrangements can be used with multispectral light assemblies, including as generally described above.

In yet another aspect, the present disclosure describes a method for controlling the amount of light from the different color channels of the illumination assembly using an illumination sensor and a feedback loop. Advantageously, in some implementations, the method can activate the separate colors sequentially and, therefore, only one color channel at a time needs to be measured by the illumination sensor and adjusted to achieve a target intensity. Accordingly, in some embodiments, the required hardware for the feedback loop may be simpler: for example, a single photo diode may be used for the illumination sensor since only one color channel is activated and measured at a time. In some embodiments, each color channel may be activated sequentially during a single exposure. In other embodiments, each color channel is activated during a separate exposure and each color channel exposure may be implemented sequentially.

FIG. 1 is a schematic block diagram of a multispectral light assembly in accordance with an embodiment of the technology. In some embodiments, a plurality of multispectral light assemblies 100 may be used in an illumination assembly of a vision system as discussed further below. In the embodiment shown in FIG. 1, the multispectral light assembly 100 includes a multispectral light source 102 and beam shaping optics 116 that include a light pipe 104, a diffusive surface 106 and a projection lens 108.

Multispectral light source 102 can include a plurality of color LED dies that generate light in multiple wavelengths. In an embodiment, the plurality of color LED dies can be provided in a single package, for example, an RGB LED, an RGBW LED, an RGB(IR) LED, an RGBY LED, other RGB LED type, an IR and Red LED, a White and Red LED, or other multi-wavelength LED type. Each LED die of the multispectral light source may be controlled independently (e.g., using a processor). In some embodiments, the multispectral light source may be an RGBW LED. An RGBW LED may be advantageous for certain applications, for example, for applications such as ID (e.g., barcode) reading when a flashing color of light is not desirable. In addition, the white LED may advantageously be used to increase the number of color channels that may be provided by the multispectral light source 102. For example, a filter may be placed on top of the white LED die of the RGBW LED package to provide the desired additional color. Alternatively, in other embodiments, a multispectral light with the additional desired color LED die may be used, for example, an RGBY LED, an RGB(IR) LED, an RGB(UV) LED, etc.

In the embodiment of FIG. 1, the light pipe 104 is positioned in front of the multispectral light source 102, along an illumination direction, and behind the diffusive surface 106 and the projection lens 108. The light pipe 104 has a length 110, an entrance surface 112 disposed proximate to the multispectral light source 102, and an exit surface 114. In some embodiments, the shape of the light pipe 104 (as illustrated in FIG. 1) may be an inverted truncated pyramid or a similar geometry. In some embodiments, the length 110 of the light pipe 104 and a ratio between the area of the entrance 112 and exit 114 surfaces can be optimized to obtain good color mixing with compact dimensions, including over a relatively short dimension in the illumination direction, as compared to conventional systems. In some embodiments, the geometry or shape of the edges of the light pipe 104 may be optimized. In some embodiments, the entrance 112 and exit 114 surfaces of the light pipe 104 may have a curved geometry. In some embodiments, the shape of the light pipe 104 may be a curved truncated pyramid. In some embodiments, the shape of the light pipe 104 may not follow a particular defined shape, for example, the shape of the light pipe 104 may be a freeform curve.

Generally, the light pipe 104 can be used to collect the maximum amount of light from the multispectral light source 102. In addition, the light pipe 104 can provide a square surface to project the light in a rectangular area and may be used to correct for non-uniformity caused by off-axis placement of the different color dies of the multispectral light source 102. In some embodiments, the light from the light pipe 104 may be projected in areas with other shapes such as a square. Advantageously, the light pipe 104 is configured to provide color mixing including the combination of multiple colors. Light pipe 104 can be used to homogenize the different spectrums generated by the multispectral light source 102 and also to make the mixing of color more uniform. A further advantage of using a light pipe 104 is that the light pipe 104 can enable the projection of direct light (e.g., color mixed) at longer working distances. In some embodiments, the light pipe enables the projection of light in a rectangular area that has a shape that is approximately equal to the field of view (FOV) of a camera of a vision system. As shown in FIG. 1, each multispectral light assembly 100 may include a light pipe 104. Accordingly, in a vision system with a plurality of multispectral light assemblies 100, each multispectral light assembly may include a light pipe 104. In alternative embodiments, a plurality of light pipes may be provided independently, for example, a plurality light pipes may be provided as a separate unitary structure where the light pipes are connected or coupled to each other. The light pipe structure may be removably coupled to a plurality of multispectral light assemblies. For example, an independent light pipe structure may be provided with four light pipes with four connections between the light pipes. In some embodiments, the number of light pipes in the separate, independent light pipe structure may fewer than the number of multispectral light sources in the vision system.

In some embodiments, the diffusive surface 106 may be, for example, a holographic diffuser positioned on the exit surface 114 of the light pipe 104, a diffusing pattern or texture (e.g., roughness) applied to the exit surface 114 of the light pipe 104, or a micro lenses array (MLA) in the form of foils with adhesive that may be installed on the exit surface 114 of the light pipe 104. For example, in some embodiments, the diffusive surface 106 may be formed by a holographic diffuser that may be attached to the light pipe 104 during a molding process of the light pipe 104 or may be attached to the light pipe 104 after the molding process of the light pipe 104. In another example, the diffusive surface 106 may be formed by a diffusive pattern or texture applied to the exit surface 114 of the light pipe or a diffusive pattern or texture may be formed with the light pipe 104 as one unitary piece. The diffusive surface 106 may be used to control of the shape of a transmitted light beam from the light pipe 104 and to control the angle of the light beam coming out of the light pipe 104. The diffusive surface 106 can be used to make the light pattern at the exit surface 114 of the light pipe 104 more uniform and to provide an optimized balance between uniformity and efficiency between the light pipe 106 and the projection lens 108, with noted improvement in uniformity and efficiency relative to conventional (e.g., Lambertian) diffusers. Accordingly, the diffusive surface 106 can be used to both improve and balance the efficiency and uniformity of the light pattern projected from the light pipe 104. In addition, the light pipe 104 and diffusive surface 106 may be used together to achieve advantageous color mixing properties for the different wavelengths traveling through them, with a very compact size. Advantageously, the diffusive surface 106 may be used to overcome limitations on the length of the light pipe 104, for example, the optimal length of the light pipe 104 may be too large for the overall size constraints of a vision system resulting in the use of a smaller length light pipe. In some embodiments, if there is enough space in the vision system for a light pipe with an optimal length, the exit surface 114 of the light pipe 104 may be clear or transparent without a diffusive surface.

As also shown in the embodiment of FIG. 1, the projection lens 108 may be positioned in front of the light pipe 104 and diffusive surface 106. In an embodiment, the projection lens 108 can finally project the diffusive surface 106 on to the target area. In some embodiments, to further reduce the size of the multispectral light assembly 100 (and the overall size of the vision system) the projection lens 108 may be formed with a high refractive index. In addition, the size of the projection lens 108 may also be minimized by using an aspherical shaped lens. In some embodiments, the projection lens 108 may be a lens with a freeform shaped geometry. Advantageously, a freeform sharped geometry lens can allow for the modification of a light beam in every single point. In some embodiments, different shaped lenses may also be used for the projection lens 108 including, but not limited to, a spherical geometry, a Toroidal geometry, a cylindrical geometry and/or a combination of different geometries in a single lens. As mentioned above, the multispectral light assembly 100 may be configured to generate an illumination area shape that is approximately equal to the FOV of a camera of a vision system that includes the multispectral light assembly 100. For example, the light from the multispectral light assembly 100 may be projected efficiently in a rectangular area that follows the cone of the FOV rather than a random rectangle or round profile. In some embodiments, the light from the multispectral light assembly 100 may be projected in areas with other shapes such as a square.

In an embodiment, the combination the light pipe 104 and an aspherical projection lens 108 can allow for effectively imaging the exit 114 of the light pipe 104 onto the target (e.g., a rectangular illumination area). Advantageously, the combination of the light pipe 104, diffusive surface 106 and projection lens 108 can enable uniform color mixing with compact dimensions of the beam shaping optics 116. In some embodiments, the total track of the multispectral light assembly from the multispectral light source 102 to the vertex of the projection lens 108 may be about 25 mm. In some embodiments, the total track of the multispectral light assembly from the multispectral light source 102 to the vertex of the projection lens may be larger or smaller than 25 mm. In addition, the combination of the light pipe 104, diffusive surface 106 and projection lens 108 can enable a longer working distance and more directed light. In some embodiments, the light distribution and color mixing in the projected illumination area of the multispectral light assembly 100 may be configured for a working distance of 300-1000 mm. In some embodiments, the light distribution and color mixing in the projected illumination area of the multispectral light assembly 100 may be configured for a working distance less than 300 mm or greater than 1000 mm. Accordingly, various embodiments of the multispectral light assembly 100 may advantageously be used for a wide range of different working distances. In some examples, the working distance may be 100-300 mm, 300-500 mm, 800-1000 mm, or 1000-1200 mm. Although the illustrated arrangement of the multispectral light assembly 100 can be advantageous, including for reasons discussed above, other configurations are also possible, including configurations in which one or more of the light pipe 104, the diffusive surface 106, or the projection lens 108 are differently configured, differently arranged, or omitted.

Figure 2:
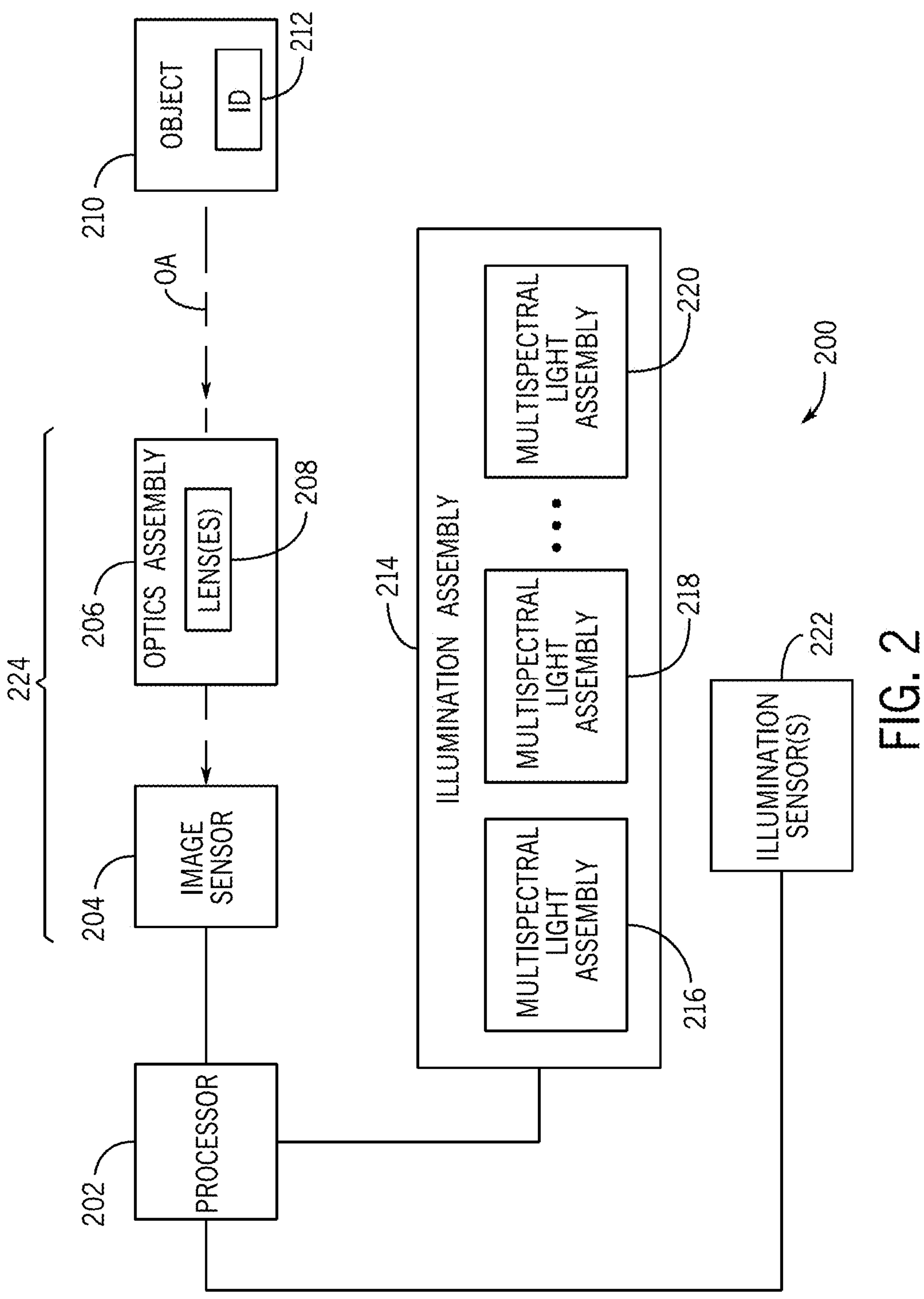
FIG. 2 is a schematic block diagram of vision system with a plurality of multispectral light assemblies in accordance with an embodiment of the technology.

As mentioned above, a plurality of multispectral light assemblies (e.g., of the multispectral light assemblies 100) may be used in an illumination system of a vision system. FIG. 2 is a schematic block diagram of vision system 200 with a plurality of multispectral light assemblies in accordance with an embodiment of the technology. While FIG. 2 illustrates an embodiment of a vision system arrangement, it should be understood that the various embodiments described herein may be implemented on different types of vision systems including, but not limited to, mobile (e.g., hand held) or fixed mount ID readers, inspection systems, etc. It should be noted that the depicted arrangement of components is illustrative of a wide range of layouts and component types. The illustrated embodiment is thus provided to teach a possible arrangement of components that provide the functions of the illustrative embodiment, although other embodiments can exhibit other configurations.

The vision system 200 shown in FIG. 2 includes an illumination assembly 214, and a vision camera assembly 224 that includes an image sensor 204 and an optics assembly 206. The vision system 200 can be used to acquire an image of an object 210 or an exemplary ID (e.g., a barcode) 211 on the object 210. The vision system 200 also includes processing components (e.g., processor 202) that perform various vision system tasks such as ID code finding and decoding, inspection, etc. The illumination assembly 214 may include a plurality of multispectral light assemblies 216, 218, 220. Each of the multispectral light assemblies 216, 218, 220 may be, for example, an identical or varied implementation of the multispectral light assembly 100 as described above with respect to FIG. 1. While three multispectral light assemblies are shown, it should be understood that different numbers of multispectral light assemblies may be used in the illumination assembly 214 in other embodiments (e.g., two, four, eight, sixteen, etc.).

As described above relative to the assembly 100, for example, each multispectral light assembly 216, 218, 220 can include a multispectral light source, a light pipe, a diffusive surface and a projection lens 108. The plurality of multispectral light assemblies 216, 218, 220 in the illumination assembly 214 may be used to generate light in multiple wavelengths that may be projected onto the object 210 to, for example, acquire an image of the object 210 or an image or the ID 212 on the object. As discussed further below, in some embodiments, different wavelengths (i.e., color channels) can be activated sequentially or according to other control strategies.

In some embodiments, the plurality of multispectral light assemblies 216, 218, 220 are positioned symmetrically around the camera lens (e.g., lens(es) 208 of the optics assembly 206). For example, light assemblies or banks of light assemblies can be distributed at regular intervals around a lens or in a balanced configuration on multiple sides of a lens. In addition, the orientation of the color LED dies of the multispectral light source in each multispectral light assembly may be arranged to provide the desired uniformity, including as further discussed below. The illumination assembly 214 may advantageously be used to project direct light (e.g., color mixed) into a well-defined and uniformly illuminated area on the object 210, for example, an illuminated area that has a shape that is approximately equal to the field of view (FOV) of the vision camera 224. In some embodiments, the illuminated area may be a rectangular area. In some embodiments, the illuminated area may have other shapes such as a square.

As mentioned, the vision system 200 can be used to acquire an image of the object 210 or the exemplary ID 212, for example, in the form of a barcode, on the object 210. An image may be acquired by projecting an illumination light on the object 210 and receiving reflected illumination light from the object 210. Thus, in front of the image sensor 204 is placed an optics assembly 206 having a series of lenses 208 that project the images light onto the area of the image sensor 204 and, correspondingly, define a FOV for imaging with the image sensor 204. In an embodiment, the optics assembly 206 may include one or more liquid lenses, as may allow for rapid and automated adjustment of focus for images at different working distances. In other embodiments, the optics assembly 206 can include a lens assembly 208 with mechanical parts (e.g., gear, motor and thread assembly) that are used to move a lens toward or away from the image sensor 204 to change the focal distance of the system 200 Light projected from the illumination assembly 214 that is reflected from the object 210 back to the vision system 200 is directed through the lens(es) 208 along a reader optical axis OA to the image sensor 204. The image sensor 204 can be configured to detect different wavelengths of light. In some embodiments, the image sensor 204 may be monochromatic sensor (e.g., black and white) or a color sensor. The reflected light is received by the image sensor 204 for processing (e.g., by processor 202) to, for example, generate an image of the subject. Known methods may be used for generating an image of the scene and decoding data therein.

The processor 202 can control vision system analysis processes (e.g., ID reading and decoding, inspection) as well as other functions, including projection of an aimer beam, illumination for image acquisition (e.g., timing or intensity of illumination, selection of a light source for illumination, etc.), automatic focus adjustment, etc. In some embodiments, the processor 202 can include one or more processor devices that can be provided on one or more circuit boards and operatively interconnected by the appropriate ribbon cable(s) or other communication channels (not shown). The system 200 may also be configured to wirelessly transmit (via a wireless link, not shown) decoded data to a data handling device such as an inventory tracking computer or logistics application. Alternatively, the system 200 may be wired to a data handling device/network or can store and subsequently transfer collected information when it is connected to a base unit. The processor 202 may be in communication with the image sensor 204, the illumination assembly 214, as well as a variety of other components (not shown), such as motors for an adjustment of system orientation, or a variety of other actuators.

In some embodiments, the vision system 200 also includes an integrated (e.g., internal) illumination sensor 222 that is in communication with the processor and, for example, located proximate to the multispectral light assemblies 216, 218, 220 of the illuminations assembly 214. In an embodiment, the illumination sensor 222 may be integrated into the illumination assembly 214. The illumination sensor 222 and the processor 202 can implement a feedback loop that may be used to control the amount of light of the different color channels projected by the illumination assembly 214 and thereby improve image acquisition. In some embodiments, the illumination sensor 222 may advantageously be located proximate to or near the multispectral LEDs in the vision system 200. For example, the illumination sensor 222 may be located at a PCB level (printed circuit board) of the vision system 200 and collect light from the LEDs of the multispectral light assemblies 216, 218, 220. In some embodiments, a plurality of illumination sensors 222 may be located higher in the structure of the vision system 200, for example, proximate to or near the lenses (e.g., lens 108) of each multispectral light assembly 216, 218, 220 and a far end of the vision system 200. In this embodiment, it is advantageous to include a plurality of illumination sensors 222 because it may be possible that not all of the subsystems of the vision system 200 may perform with the same efficiency. The illumination sensors 222 can be coupled to the PCB of the vision system 200 and located at a particular height.

For example, as also discussed further below, part of the light transmitted through one or more light pipes of one more multispectral light assemblies 216, 218, 220 can be diverted onto, or otherwise received by, the illumination sensor 222, which can then measure the intensity of the light. As appropriate, the measured intensity can be used to control the amount of light (intensity and/or LED on-time) for each of the wavelengths (a.k.a. color channels). Advantageously, in some embodiments, each wavelength or color channel is activated sequentially so that only one channel is on (i.e., illuminating a target for imaging) at any time. Accordingly, the illumination sensor 222 only needs to measure one color channel at a time and the illumination sensor 222 may be, for example, a single photo-diode that may be used to measure each of the colors. As each color channel is on, the intensity or an exposure time can be adjusted until a target amount of light or exposure (i.e., the product of the intensity and exposure duration (or exposure time or LED on-time)) is reached. Once the target exposure (or amount of light) is reached for a particular color channel, the channel can be turned off, and the next color channel can be turned on (as appropriate). In an embodiment, the feedback loop and exposure adjustment may be repeated for each color channel as each channel is sequentially activated.

In some embodiments, each wavelength or color channel may be activated simultaneously so that all channels are on (i.e., illuminating a target for imaging) at the same time. Accordingly, in some embodiments, the illuminations sensor 222 may include a plurality of illumination sensors and each illumination sensor may be configured to measure one of the color channels. For example, each illumination sensor 222 may be, for example, a photodiode configured to measure one of the colors. In some embodiments, for simultaneous illumination with a plurality of colors channels, the illumination sensor 222 may be a single illumination sensor 222 (e.g., a photodiode) configured to measure all of the color channels simultaneously. In some embodiments with simultaneous activation of each wavelength or color channel, color mixing may be performed and colors beyond those installed on a system (e.g., the system shown in FIG. 2) may be measured. As mentioned above, the intensity or an exposure time of each color channel can be adjusted until a target amount of light or exposure (i.e., the product of the intensity and exposure duration (or exposure time or LED on-time)) is reached. Once the target exposure (or amount of light) is reached for a particular color channel, the channel can be turned off.

As mentioned above, the orientation of the color LED dies of the multispectral light source in each multispectral light assembly may be arranged to provide the desired uniformity. In some embodiments, each of the color LED dies can include multiple lighting positions (e.g., in a quadrant arrangement), and a beneficial lighting uniformity can be obtained by collectively balancing the distribution of illumination sources for particular colors relative to lighting positions in each of the multispectral light sources. For example, where each multispectral light source of a plurality of multispectral light sources includes a plurality of light positions, with a common spatial arrangement, the same number of LEDs of a particular color can be provided in each of the light positions, when all of the light positions of the plurality multispectral light sources are considered collectively.

Figure 3:
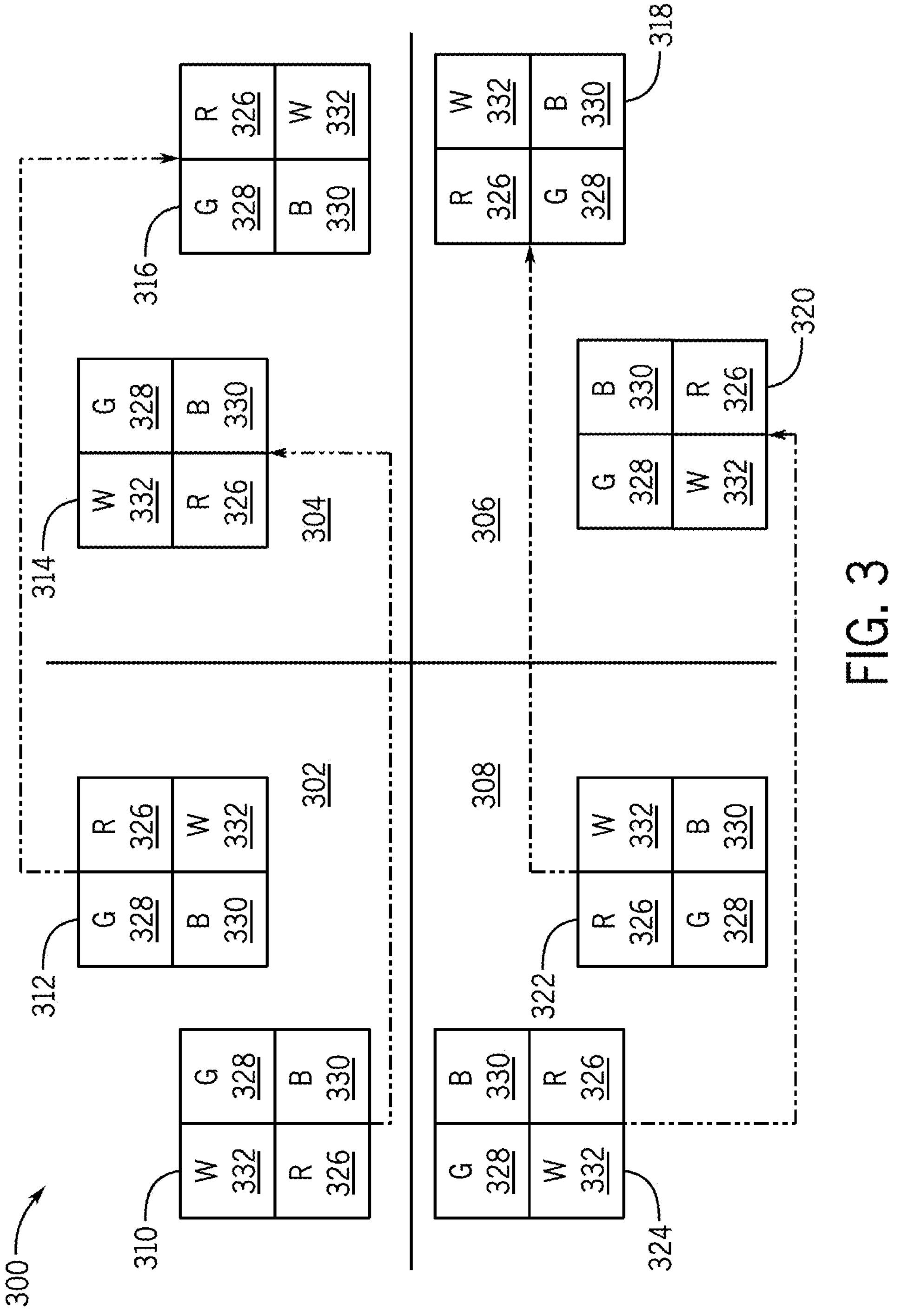
FIG. 3 is a diagram illustrating an example orientation of a plurality of multispectral light sources for an illumination system in accordance with an embodiment of the technology.

Further in this regard, for example, FIG. 3 is a diagram illustrating an example orientation of a plurality of multispectral light sources for an illumination system in accordance with an embodiment of the technology. In this example, eight multispectral light sources 310, 312, 314, 316, 318, 320, 322 and 324 are shown, however, in other embodiments, the illumination assembly may comprise different numbers of multispectral light sources (and the associated multispectral light assemblies). In the illustrated embodiment of FIG. 3, each multispectral light source 310-324 is an RGBW LED, however, it should be understood that other multispectral LEDs may be used, for example, RGB, RGB(IR), RGBY, RGB(UV), etc. Each multispectral light source 310-324 contains one each of the color LED dies Red (R) 326, Green (G) 328, Blue (B) 330 and White (W) 332. The color LED dies 326-332 of each RGBW LED 310-324 are off-axis and, therefore, it is advantageous to provide the dies in an orientation that is as symmetric as possible to provide the desired uniformity. In the example orientation shown in FIG. 3, the light from the illumination assembly is divided into four quadrants, namely a first quadrant 302, a second quadrant 304, a third quadrant 306 and a fourth quadrant 308. Considering the lighting array collectively, two of the eight RGBW LEDS 310-324 are positioned in each quadrant 302-308 so as to be symmetrically positioned around a camera axis. Namely, RGBW LEDs 310 and 312 are located in the first quadrat 302, RGBW LEDs 3114 and 316 are located in the second quadrant 304, RGBW LEDs 318 and 320 are located in the third quadrant 306 and RGBW LEDs 322 and 324 are located in the fourth quadrant 308. In another embodiment with 16 RGBW LEDs, four RGBW LEDS would be positioned in each quadrant.

Further, in the illustrated example, each color LED die 326-332 is present in the same position and orientation (i.e., in the same lighting position for the given LED die) two times, as indicated by the dashed line arrows, to provide a balanced distribution of color. Although a variety of approaches can provide this result, in the illustrated example, the color LED die orientation is the same for RGBW LED 310 and RGBW LED 314; for RGBW LED 312 and RGBW LED 316; for RGBW LED 318 and RGBW LED 322; and for RGBW LED 320 and RGBW LED 324. Advantageously, the light pattern of the multispectral light sources 310-324 can be more square and uniform, as compared to conventional lighting systems, because the color LED dies 326-332 are covering each quadrant and because the lighting positions of the differently colored LEDs, within the larger LED dies, are collectively balanced.

In other embodiments, each possible color LED die orientation may be provided in each quadrant. In yet another embodiment, the illumination system includes four multispectral light sources (and, therefore, four multispectral light assemblies) and one multispectral light source is located in each quadrant. In this latter embodiment, for example, the red LED die of each multispectral light source may be located at each corner of each quadrant to provide symmetry. Further, although the illustrated configuration of color LED dies can be advantageous, including for reasons discussed above, other configurations are also possible.

Figure 4:
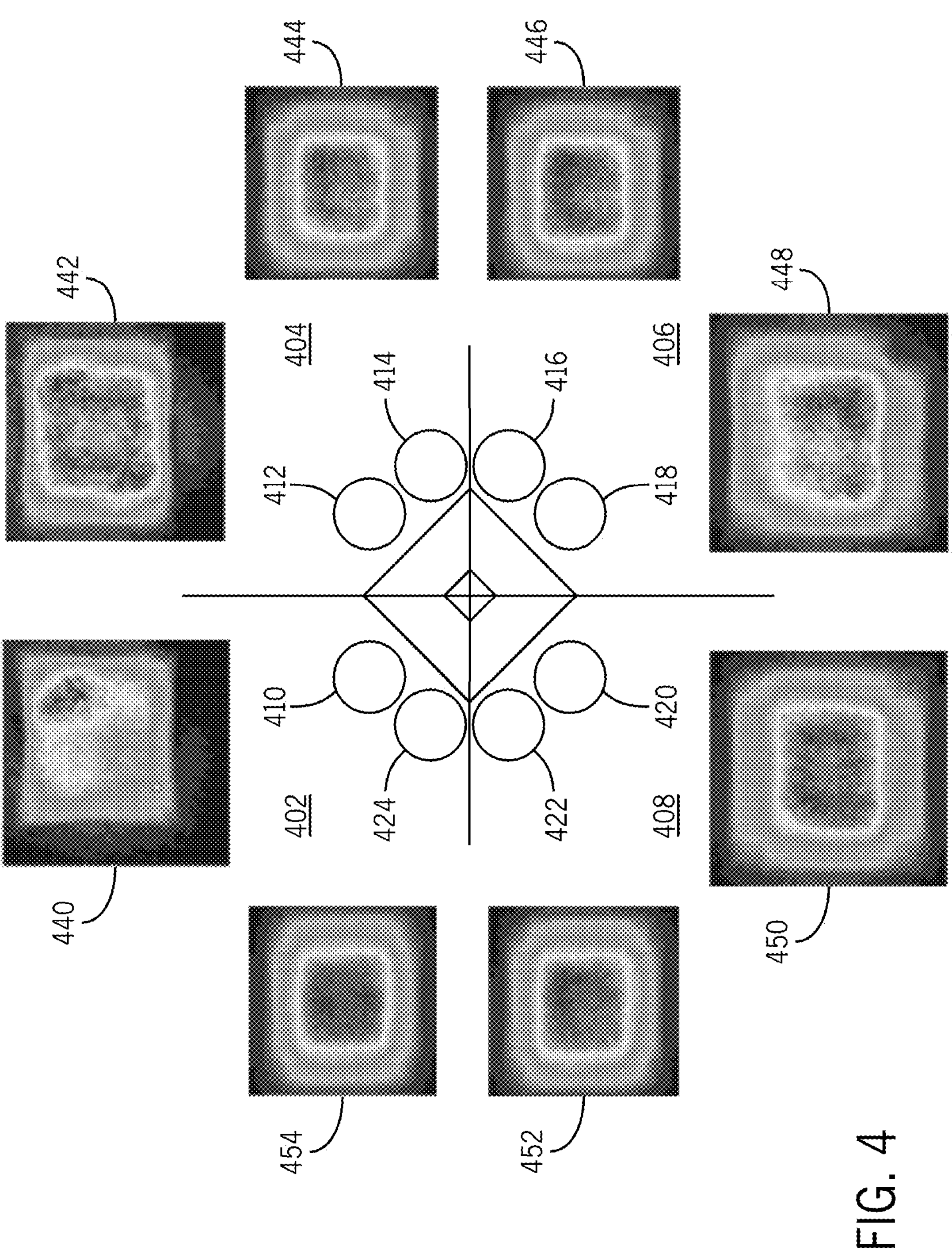
FIG. 4 illustrates example illumination light patterns generated using various combinations of illumination from multispectral light assemblies in an illumination system in accordance with an embodiment of the technology.

In some embodiments, various combinations of the multispectral light assemblies may be activated to provide the illumination light. FIG. 4 illustrates example illumination light patterns generated using various combinations of illumination from multispectral light assemblies in an illumination system in accordance with an embodiment of the technology. The example illumination system used to generate the illumination light patters shown in FIG. 4 includes eight multispectral light sources 410-424 (and the associated multispectral light assemblies) that are positioned symmetrically around a camera axis. For this example, the multispectral light sources were RGBW LEDs. A first illumination pattern 440 was generated using a first north RGBW LED located in the first quadrant. The remaining illumination patters 442-454 represent the illumination pattern generated by adding on an additional RGBW LED 412-424, respectively, one at a time moving clockwise.

In this regard, it can be seen that the illumination pattern 442 generated with the first north RGBW LED and second north RGBW LED 412 has improved uniformity of the illumination as compared to the illumination pattern 440. However, image acquisition may still be sub-optimal, including if the image sensor (e.g., image sensor 204 shown in FIG. 2) of the vision system is a linear sensor. For example, a central area of the illumination pattern 442 generated by the north bank of RGBW LEDS 410, 412 may be of deficient intensity towards the bottom side of the central imaging area.

Continuing, the illumination pattern 446 was generated using four of the RGBW LEDS 410, 412, 414, and 416, has acceptable uniformity, however, it is not as bright as if all of the RGBW LEDS 410-424 are used to generate the illumination as shown by illumination pattern 454. Thus, for example, by utilizing all of the multi-spectral light sources 410-424, as shown via the illumination pattern 454, a bright, highly uniform, symmetrical, square pattern can be obtained. Accordingly, in some embodiments, different combinations of the multispectral light source may be utilized to generate the illumination based on the requirements of the application of the vision system. In some cases, a beneficial balancing of light sources of different colors (e.g., as discussed relative to FIG. 3) can be implemented in combination with the illumination strategy discussed relative to FIG. 4, with particularly beneficial results. However, other distributions of differently colored illumination sources can also be used.

Figure 5:
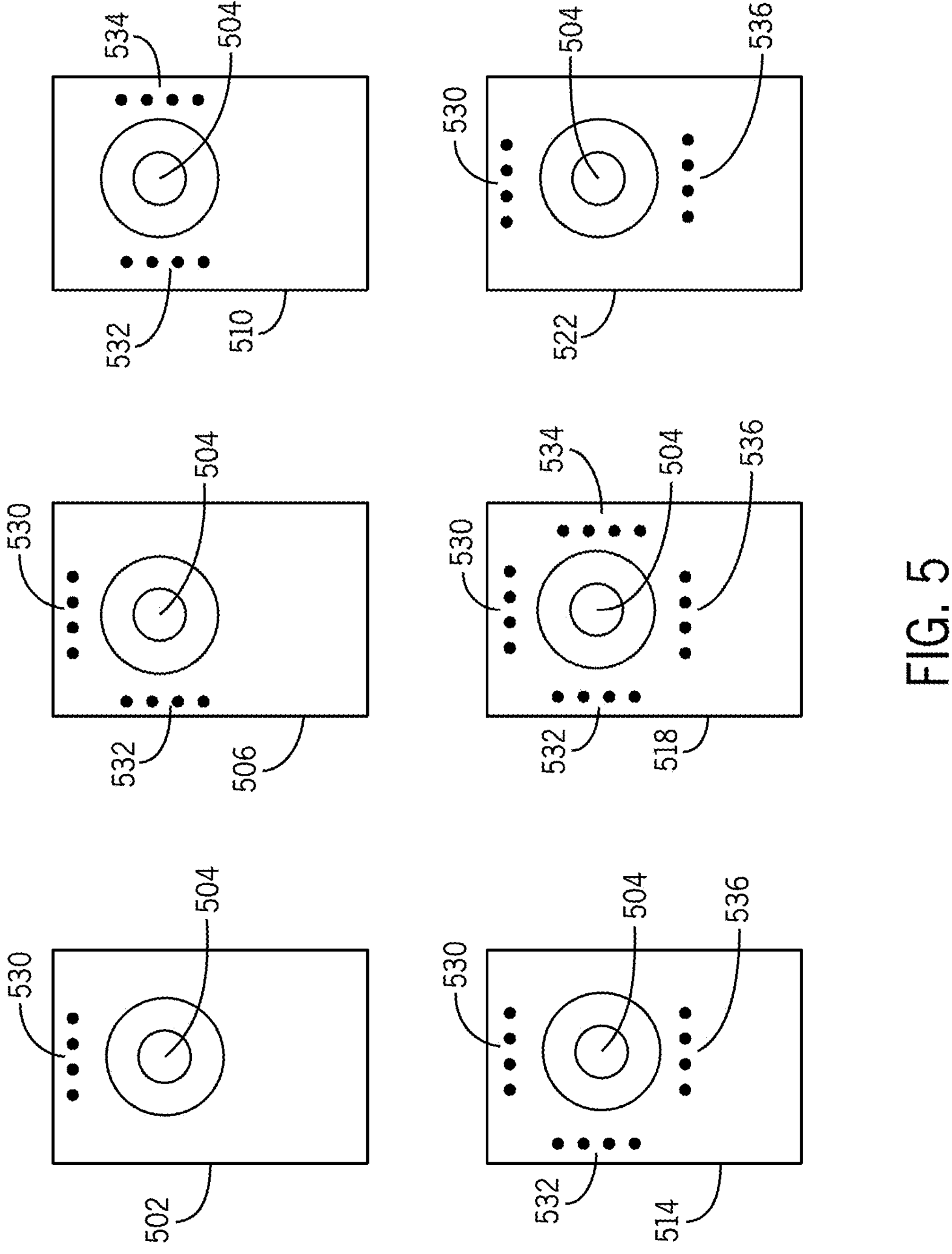
FIG. 5 is a schematic diagram showing example light banking configurations of an illumination system in accordance with an embodiment of the technology.

FIG. 5 is a schematic diagram showing example light banking configurations of an illumination system in accordance with an embodiment of the technology. In some embodiments, different light banking configurations may be used to provide the illumination light for different applications. For example, light banking configurations of multispectral light sources may be used for applications such as to provide good lighting conditions for surface features detection algorithms such as, for example, surface FX feature extraction technology, to provide low angle light effect, or to provide color light banking. Advantageously, a set or array of multispectral light sources (e.g., RGBW LEDs) may be selected in different configurations (e.g., in North, South, East, and West quadrants). For example, selecting a particular set (e.g., array) of LEDs in one or more particular quadrants to generate the illumination (e.g., quadrants 302-308 shown in FIG. 3) can provide benefits including uniformity within the quadrant, e.g., if it is desirable to create shadows. In some embodiments, selective control of light banks can be implemented using multispectral lighting, as variously described herein. However, other lighting configurations are also possible.

In FIG. 5, six example light banking configurations are shown, as may correspond to control of lighting for six different image acquisitions (e.g., six different exposures). A first example configuration 502 includes illumination of a bank of multispectral light sources 530 that are positioned north of a camera axis 504 of the vision system. A second example configuration 506 includes illuminating the bank of multispectral light sources 530 and a bank of multispectral light sources 532 positioned west of the camera axis 504 of the vision system. A third example configuration 510 includes illuminating the bank of multispectral light sources 532 and a bank of multispectral light sources 534 positioned east of the camera axis 504 of the vision system. A fourth example configuration 514 includes illuminating the bank of multispectral light sources 530, the bank of multispectral light sources 532 and a bank of multispectral light sources 536 positioned south of the camera axis 504 of the vision system. A fifth example configuration 518 includes illuminating the bank of multispectral light sources 532, the bank of multispectral light sources 534, the bank of multispectral light sources 534 and the bank of multispectral light sources 536. A sixth example configuration includes illuminating the bank of multispectral light sources 530 and the bank of multispectral light sources 536. Although the illustrated light banking configurations can be advantageous, other configurations are also possible.

In some embodiments, each bank of multispectral light sources (e.g., the "north" bank (or quadrant) 530, the "west" bank (or quadrant) 532, the "east" bank (or quadrant) 534, and the "south" bank (or quadrant) 536 shown in FIG. 5) may be used to provide illumination in one of the colors of the LED's included in each multispectral light source in the bank. For example in the second example configuration 506, a red LED of each multispectral light source in the "north" bank 530 may be activated to provide red illumination light from the "north" bank 530 and a green LED of each multispectral light source in the "west" bank 532 may be activated to provide green illumination light from the "west" bank 532 In another example, in the fourth example configuration 514, a green LED of each multispectral light source in the "north" bank 530 may be activated to provide green illumination light from the "north" bank 530, a blue LED of each multispectral light source in the "west" bank 532 may be activated to provide blue illumination light from the "west" bank 532, and a red LED of each multispectral light source in the "south" bank 536 may be activated to provide red illumination light from the "south" bank 536. In some embodiments, two or more banks of multispectral lights may be used to provide the same color illumination light. During operation of the illumination system, the color of the illumination light provided by a bank of multispectral light sources may be changed by changing the color LED activated in each multispectral light source. For example, the "north" bank 530 may be changed from a red illumination light to a blue illumination light by changing the LED activated in each multispectral light source of the "north" bank 530 from a red LED to a blue LED.

Figure 6:
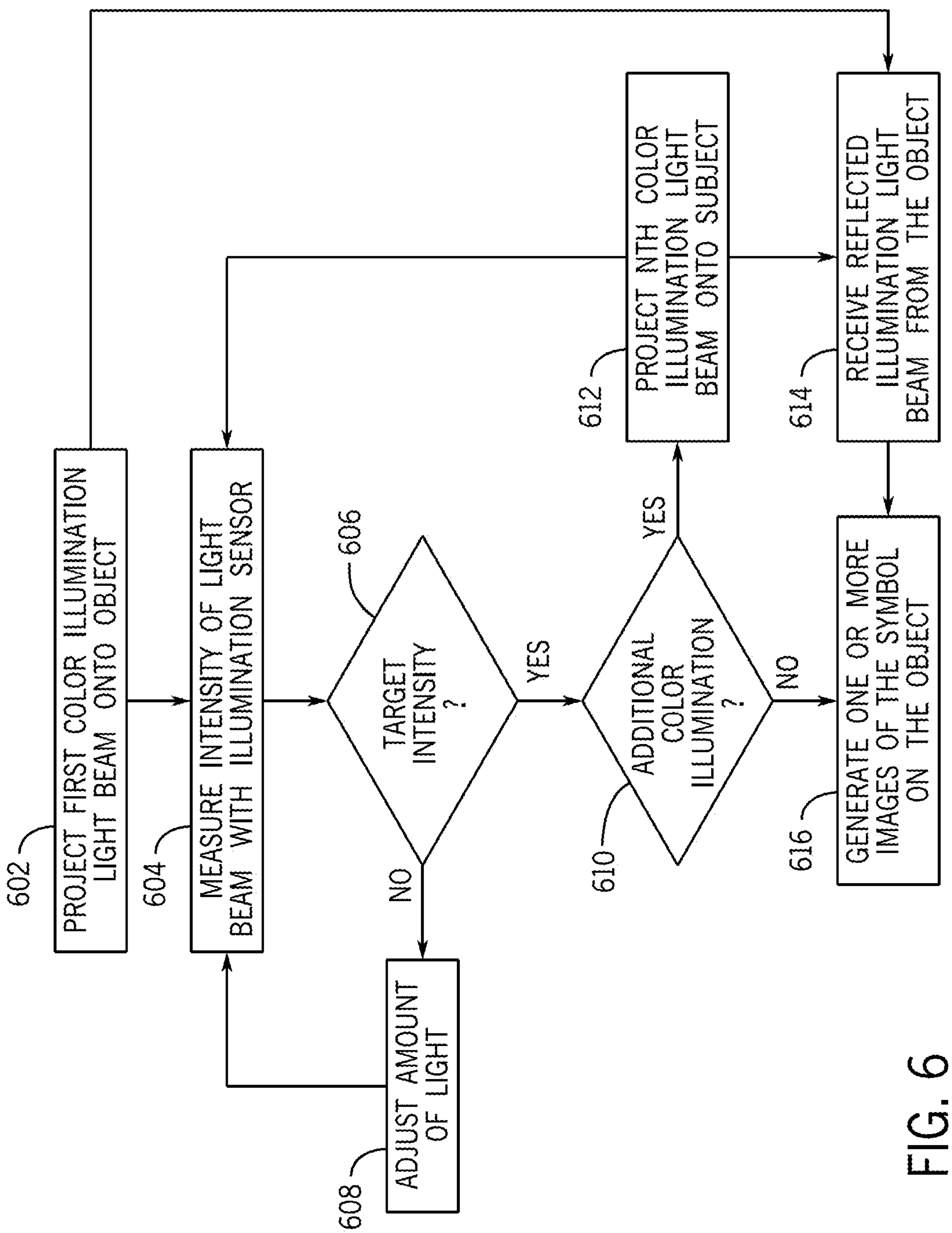
FIG. 6 illustrates a method for controlling an illumination system with multispectral light assemblies for generating an image in accordance with an embodiment of the technology.

FIG. 6 illustrates a method for controlling an illumination system with multispectral light assemblies for generating an image in accordance with an embodiment of the technology. As mentioned above with respect to FIG. 2, the amount of light from the different color channels generated by the multispectral light assemblies in the illumination system may be controlled using an illumination sensor (e.g., illumination sensor 222 shown in FIG. 2) and a processor (e.g., processor 202 shown in FIG. 2) to form a feedback loop. In some embodiments, the color channels are advantageously activated sequentially. For example, a separate exposure may be used for each sequentially activated color channel or each color channel can be activated sequentially during the same single exposure.

In one example, at block 602, a first color illumination light beam is projected onto an object by activating, for example, a corresponding color LED die of one or more multispectral light assemblies (e.g., multispectral light assembly 100 shown in FIG. 1). In some embodiments, the light beam may be a single color (e.g., may be generated by only LEDs of a single color). At block 604, the intensity of the generated color illumination light beam is measured using an illumination sensor (e.g., illumination sensor 222 shown in FIG. 2). For example, part of the color illumination light transmitted from one more multispectral light assemblies can be diverted onto the illumination sensor that then measures the intensity of the light. In some embodiments, the illumination sensor may be a photo-diode, which may not be particularly tuned to any given color of light.

At block 606, it is determined (e.g., by a processor device) whether the measured intensity is sufficient, e.g., whether the measured intensity generates a target exposure or amount of light (i.e., the product of the measured intensity and the exposure time) or whether the integrated intensity for the color over a particular time (e.g., within the current exposure) is sufficient. If the measured intensity at block 604 is not sufficient to generate the target exposure, the amount of light (e.g., intensity or duration of illumination of the color LED die(s)) is adjusted at block 608. Or, if the total intensity over time is not sufficient, a length of an exposure for that color of light may be adjusted (e.g., extended). In some embodiments, the intensity of the light beam will continue to be measured, and corresponding adjustments made, until the intensity is sufficient (e.g., the current intensity or the intensity over time generates the target exposure (or amount of light)).

In some embodiments, as also noted above, adjusting an amount of light (e.g., at block 608) can include adjusting a duration of an amount of time during which a particular color of light is used to illuminate a target. For example, during an image acquisition over a single or multiple exposures, the duration of illumination for any given color of light from a multispectral illumination assembly can be determined in real time (or otherwise) by monitoring the cumulative illumination provided by that color of light and determining when the cumulative illumination is sufficient for good image acquisition.

Once the intensity of the color illumination light beam reaches the target intensity (or target exposure) at block 606, it is determined whether there are any additional color illuminations (e.g., color channels) that need to be projected on the object at block 610. The specific color channels that are projected on the object may be determined, for example, based on the specific application of the vision system. If there is an additional color illumination at block 610, the first color illumination light beam can be turned off and a second color illumination light beam (or color channel) is projected in the object at block 612 and the process move to block 604. At block 604, the intensity of the second generated color illumination light beam is measured using the illumination sensor (e.g., illumination sensor 222 shown in FIG. 2). The amount of light from second color illumination light beam is then adjusted at block 608 until it reaches the target intensity (or target exposure) at block 610.

Blocks 604-612 can be repeated, as appropriate, for each color illumination light beam, for example for N color illumination light beams, until all of the color channels have been projected at the target intensity (or target exposure). As mentioned above, the color channels may sometimes thus be activated sequentially, and in some cases a prior color channel can be turned off before the next color channel is turned on.

As the various color illumination light beams (or color channels) are projected on the object, the illumination light reflected from the object is received by the vision system and, for example, directed to an image sensor by one or more lenses at block 614 (e.g., images sensor 204 and lens(es) 208 shown in FIG. 2). Once all of the necessary color illumination light beams (or color channels) have been projected at block 610, one or more images of the object or a symbol on the object may be generated based on the received illumination light using a processor (e.g., processor 202 shown in FIG. 2) at block 616. Known methods may be used for generating an image of the object or a symbol on the object and deciding data therein. For example, a single image can be generated based on a single exposure, during which different colors of light illuminate an object at different times, or a single image can be generated as a composite of multiple exposures, during which different colors of light are used.

As mentioned above, it may be advantageous to activate each color channel sequentially so that only one channel is on at any time. Accordingly, in some embodiments, the illumination sensor only needs to measure one color channel at a time and the illumination sensor may be, for example, a single photo-diode that may be used to measure each of the color channels.

Figure 7:
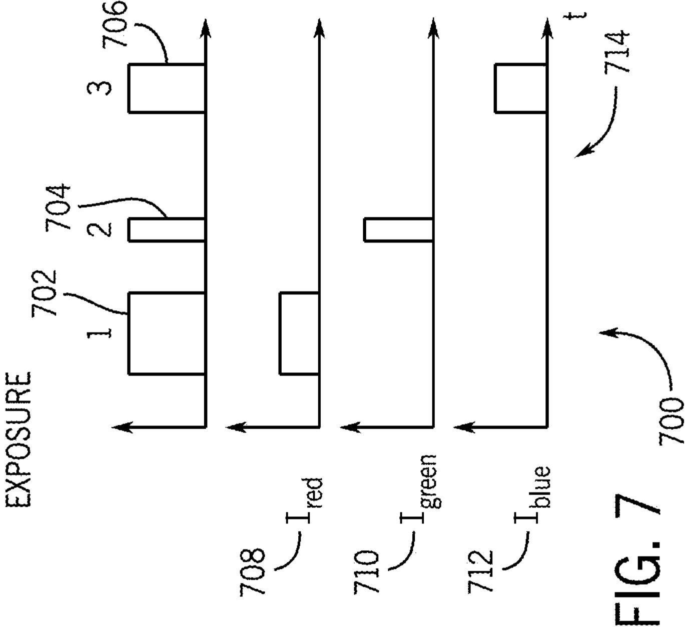
FIG. 7 is a graph illustrating a timing configuration using multiple exposures for generating an image using an illumination system with multispectral light assemblies in accordance with an embodiment of the technology.

As mentioned above, in some embodiments a separate exposure may be used for each sequentially activated color channel. FIG. 7 is a graph illustrating a timing configuration using multiple exposures for generating an image using an illumination system with multispectral light assemblies in accordance with an embodiment of the technology. The example timing configuration 700 includes three separate exposures, namely, a first exposure 702, a second exposure 704 and a third exposure 706 that occur sequentially over time as illustrated by axis 714. A first color channel 708 (e.g., red) may be activated and may be used to generate illumination light during the first exposure 702. At the completion of the first exposure 702, the first color channel 708 may be turned off and a second color channel 710 (e.g., green) may be activated and may be used to generate illumination light during the second exposure 704. At the completion of the second exposure 704, the second color channel 710 may be turned off and a third color channel 712 (e.g., blue) may be activated and may be used to generate illumination light during the third exposure 706. Each exposure may be used to generate a monochromatic image. The monochromatic images from the three different color channels may then be merged to create a full RGB (or other) image. Known methods may be used for creating a full RGB image from a plurality of monochromatic images. In some embodiments, the duration of the exposures 702, 704, 706 can be determined according to the method illustrated in FIG. 6, or as otherwise generally discussed above.

Figure 8:
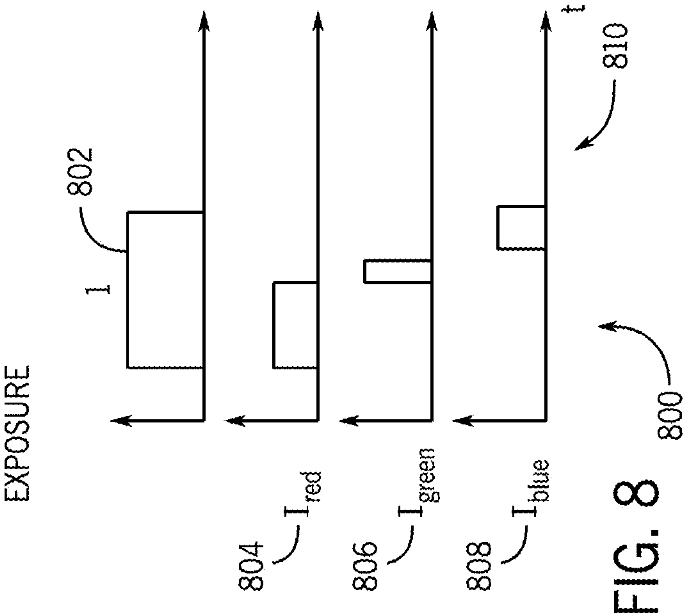
FIG. 8 is a graph illustrating a timing configuration using a single exposure for generating an image using an illumination system with multispectral light assemblies in accordance with an embodiment of the technology.

In some embodiments, each color channel can be activated sequentially during the same exposure. FIG. 8 is a graph illustrating a timing configuration using a single exposure for generating an image using an illumination system with multispectral light assemblies in accordance with an embodiment of the technology. The example timing configuration 800 includes a single exposure 802. Each color channel may be activated sequentially over time during the exposure 802 as illustrated by axis 810. A first color channel 804 (e.g., red) may be activated at a first time point and may be used to generate illumination light during the exposure 802. At the completion of a particular time period for activation of the first color channel 804, the first color channel 804 may be turned off and a second color channel 806 (e.g., green) may be activated at a second time point and may be used to generate illumination light during the exposure 802. At the completion of a particular time period for activation of the second color channel 806, the second color channel 806 may be turned off and a third color channel 808 (e.g., blue) may be activated at a third time point and may be used to generate illumination light during the exposure 802. The third color channel 808 may be activated for a particular period of time and then turned off. Thus, the three color channels 804, 806 and 810 may be mixed during the exposure 802 without actually overlapping in time. As described above with respect to FIG. 6, an illumination sensor and feedback loop may be used to control the intensity and/or the on-time of each channel 804, 806, 808 (i.e., the width of the pulses for each color channel along the axis 810) to achieve the correct color mix. Accordingly, the color mixing may be controlled during a single exposure time of the camera of the vision system. The single exposure may be used to generate a monochrome image according to any variety of known methods. However, the monochrome image may advantageously have optimized contrast for one or more of the associated colors. Further, because a single exposure can be faster than multiple separate exposures, while providing a comparable cumulative lighting intensity, the timing configuration of FIG. 8 may be advantageous for sorting applications that involve moving objects.

As mentioned above, in some embodiments, each wavelength or color channel may be activated simultaneously so that multiple channels are on (i.e., illuminating a target for imaging) at the same time. Accordingly, in some embodiments, the illuminations sensor may include a plurality of illumination sensors and each illumination sensor may be configured to measure one of the color channels. For example, each illumination sensor may be, for example, a photodiode configured to measure one of the colors. In some embodiments, for simultaneous illumination with a plurality of colors channels, the illumination sensor may be a single illumination sensor (e.g., a photodiode) configured to measure all of the color channels simultaneously. As mentioned above, the intensity or an exposure time of each color channel can be adjusted until a target amount of light or exposure (i.e., the product of the intensity and exposure duration (or exposure time or LED on-time)) is reached. Once the target exposure (or amount of light) is reached for a particular color channel, the channel can be turned off.

In some embodiments, the vision system 200 may be used with a removable diffused light assembly mounted to a housing of the vision system in front of the illumination assembly to enable the vision system to convert the illumination light to diffuse light provided at shorter distances. Accordingly, the diffused light assembly can enable the vision system 200 with multispectral light assemblies to be used with applications that require diffuse light and shorter working distances. The diffused light assembly may be advantageous for imaging for applications such as direct part marking (DPM), as well as other applications that require diffuse light. A DPM reader is capable of reading barcodes that are etched or imprinted directly onto the surface of materials such as plastics and metals. Typically, DPM parts present codes on a larger variety of geometries and surfaces.

Figures 9, 10:
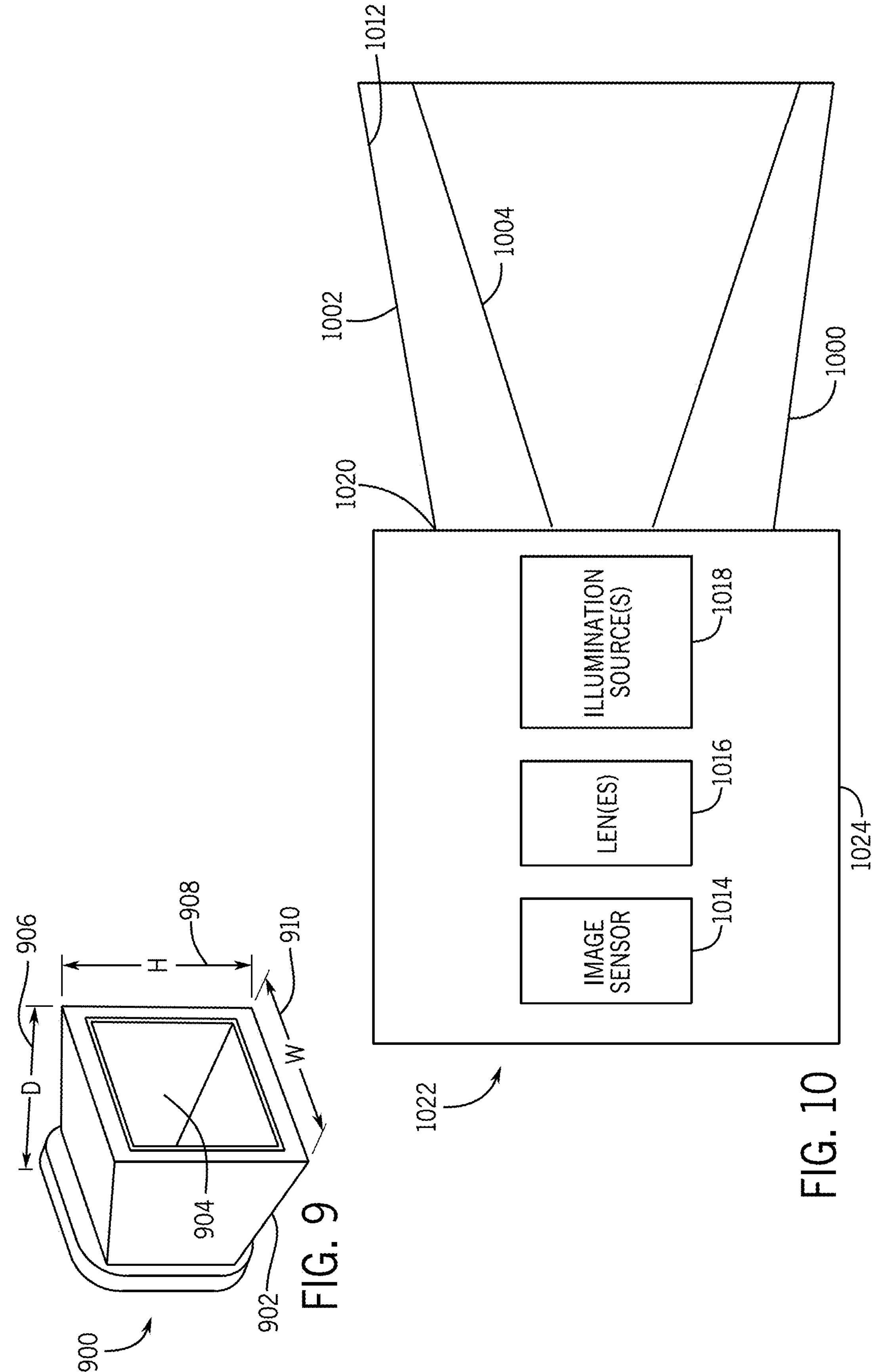
FIG. 9 illustrates an example diffused light assembly in accordance with an embodiment of the technology.
FIG. 10 is a schematic block diagram of a vision system and the diffused light assembly of FIG. 9 in accordance with an embodiment of the technology.

FIG. 9 illustrates an example diffused light assembly in accordance with an embodiment of the technology. In the embodiment illustrated in FIG. 9, a removable diffused light assembly 900 includes a housing 902 and an internal reflective surface 904. In an embodiment, the internal reflective surface 904 may include a matte white surface to assist the light traveling inside the volume of the diffused light assembly 900. Dimensions of the housing 902 (depth 906, height 908 and width 910) may be configured to allow the diffused light assembly 900 to be removably mounted to the housing of a vision system (e.g., vision system 200 shown in FIG. 2) so that the diffused light assembly 900 may be positioned in front of the vision system illumination assembly. In some embodiments, the height (H) 908 of the housing 902 is half the FOV at the near distance. The housing of the vision system may also be configured to include features to allow the diffused light assembly 900 to be attached to the vision system. Although the illustrated arrangement of the diffused light assembly 900 can be advantageous, including for reasons discussed above, other configurations are also possible.

FIG. 10 is a schematic diagram of a vision system and a diffused light assembly (e.g., similar to the assembly 900 of FIG. 9) in accordance with an embodiment of the technology. In FIG. 10, a diffused light assembly 1000 may be removable mounted or attached to a visions system 1022. For example, a housing 1002 of the diffused light assembly 1000 may be attached to a housing 1024 of the vision system using a mechanical attachment mechanism at a mechanical connection point 1020. Known mechanical attachment mechanisms may be used to removably attach the housing 1002 of the diffused light assembly 1000 to the housing of the vision system 1024. As mentioned above, the diffused light assembly 1000 may be attached to the vision system housing 1024 so that the diffused light assembly 1000 is positioned in front of an illumination assembly 1018 of the visions system 1022 (e.g., a multispectral illumination assembly, as generally described above). In some embodiments, the diffused light assembly 1000 may be a passive accessory that does not require electrical connections or additional communication with a camera of the visions system 1022. Vision system 1022 may also include an image sensor 1014 and lens(es) 1016, in addition to other components used to image a symbol or ID on an object.

In the illustrated embodiment, diffused light assembly 1000 includes a housing 1002 that has an internal reflective surface 1012 (e.g., internal reflective surface 904 shown in FIG. 9) and also includes a diffuser 1004. In some embodiments, the diffuser may be formed from a material (e.g., a milky white material) for which both translucency and texture may be defined to deliver light in the desired manner. The diffuser 1004 can provide an aperture in front of the imaging lens(es) 1016 of the vision system 1022. In some embodiments, the size of the aperture may be optimized to create the minimum impact on the even illumination produced by the diffused light assembly 1000. The diffused light assembly can be configured to create the effect of a dome light between the internal reflective surface 1012 and the diffuser 1004. Advantageously, the removable diffused light assembly may be used with different lenses (FOVs), illumination beams, light banks, and colors. The diffused light assembly 1000 can improve performance by providing a uniform light pattern for every position of the focus plane over a certain working range (e.g., 0-100 mm for factory automation DM applications). Although the illustrated arrangement of the diffused light assembly 1000 can be advantageous, including for reasons discussed above, other configurations are also possible.

Figure 11:
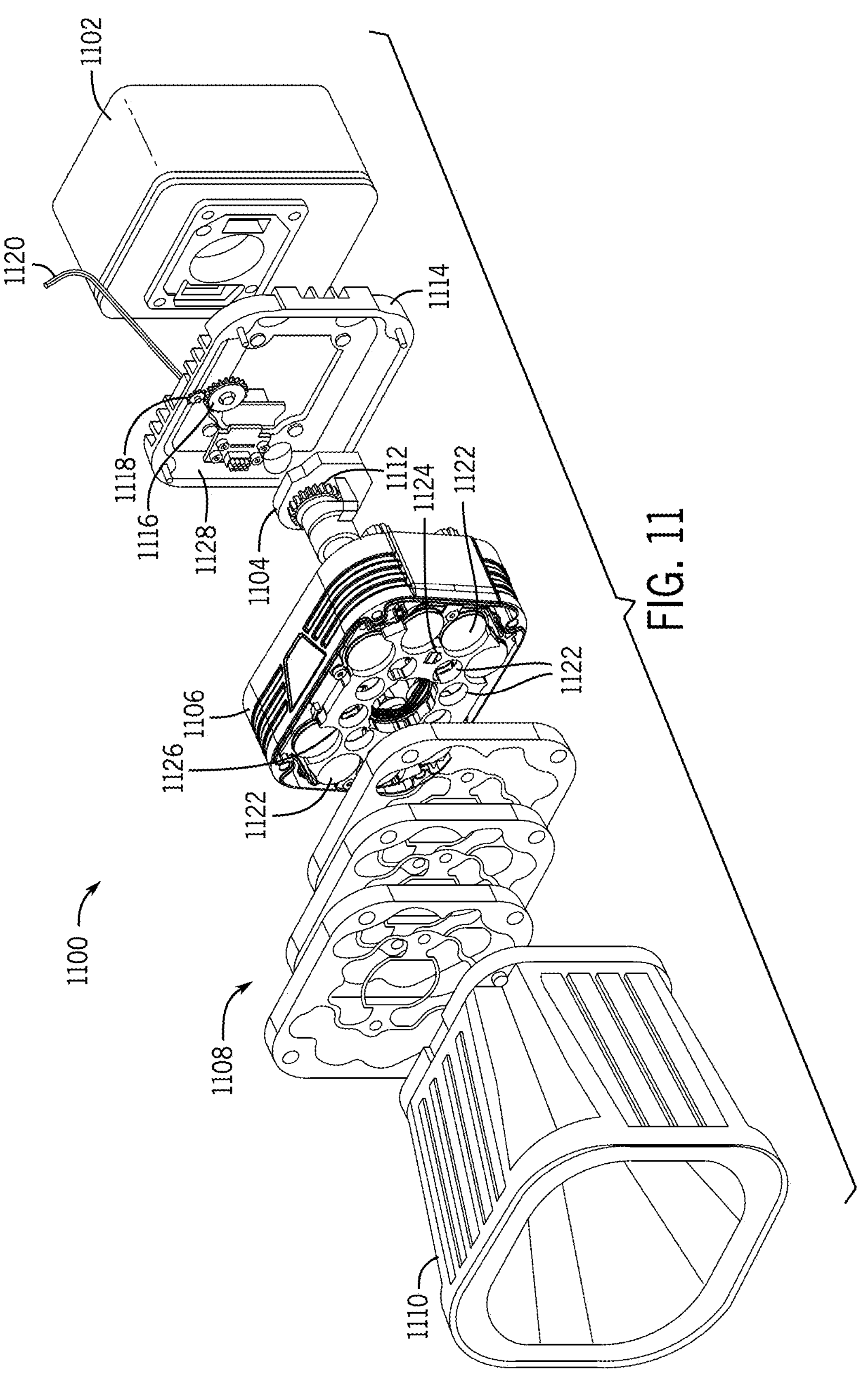
FIG. 11 is an exploded perspective view of a vision system assembly including a plurality of multispectral light assemblies in accordance with an embodiment of the technology.

FIG. 11 is an exploded perspective view of a vision system assembly including a plurality of multispectral light assemblies in accordance with an embodiment of the technology. The vision system assembly 1100 can be used to acquire an image of an object (not shown) or an ID on the object. In the illustrated vision system assembly 1100 of FIG. 11, a lens assembly 1104 is positioned in front of and, when assembled, coupled to an image sensor assembly 1102. The image sensor assembly 1102 can include an image sensor that can be configured to detect different wavelengths of light. In some embodiments, the image sensor of the image sensor assembly 1102 can be a monochrome sensor (e.g., black and white) or a color sensor. In some embodiments, the image sensor of the image sensor assembly 1102 can have a size between 2-16 mega-pixels.

As discussed above, the lens assembly 1104 may project an image's light onto an area of the image sensor of the image sensor assembly 1102 and, correspondingly, define a FOV for imaging with the image sensor of the image sensor assembly 1102. In some embodiments, the lens assembly 1104 can include one or more lenses such as, for example, a high speed liquid lens, to allow for rapid and automated adjustment of focus for images at different working distances. In other embodiments, the lens assembly 1104 can include one or more solid (e.g., glass) lenes.

In some embodiments, the vision system assembly 1100 may include mechanical parts (e.g., a gear mechanism) that can be used to manually adjust the focus of the lens assembly 1104 by moving the lens assembly 1104 towards or away from the image sensor assembly 1102 to change the focal distance of the system 1100. For example, as shown in FIG. 11, a gear mechanism can include a first gear 1112 on the lens assembly 1104, a second gear 1116 on an inside surface 1128 of a back plate 1114 of an illumination assembly 1106, and a third gear 1118 on an inside surface 1128 of a back plate 1114 of an illumination assembly 1106. As discussed further below with respect to FIGS. 13, 14 and 15, a focal adjustment tool 1120 (e.g., an Allen wrench or other known hand tool) may be used by an operator to manually drive the third gear 1118 and second gear 1116 which in turn can drive the first gear 1112 on the lens assembly to move the lens assembly 1104 or one or more glass lenses within the lens assembly 1104. In some embodiments, the one or more glass lenses may be provided with motorized mechanical parts (e.g., gear, motor and thread assembly) that are used to move a one or more lenses toward or away from the image sensor assembly 1102 to change the focal distance of the system 1100.

Figure 15:
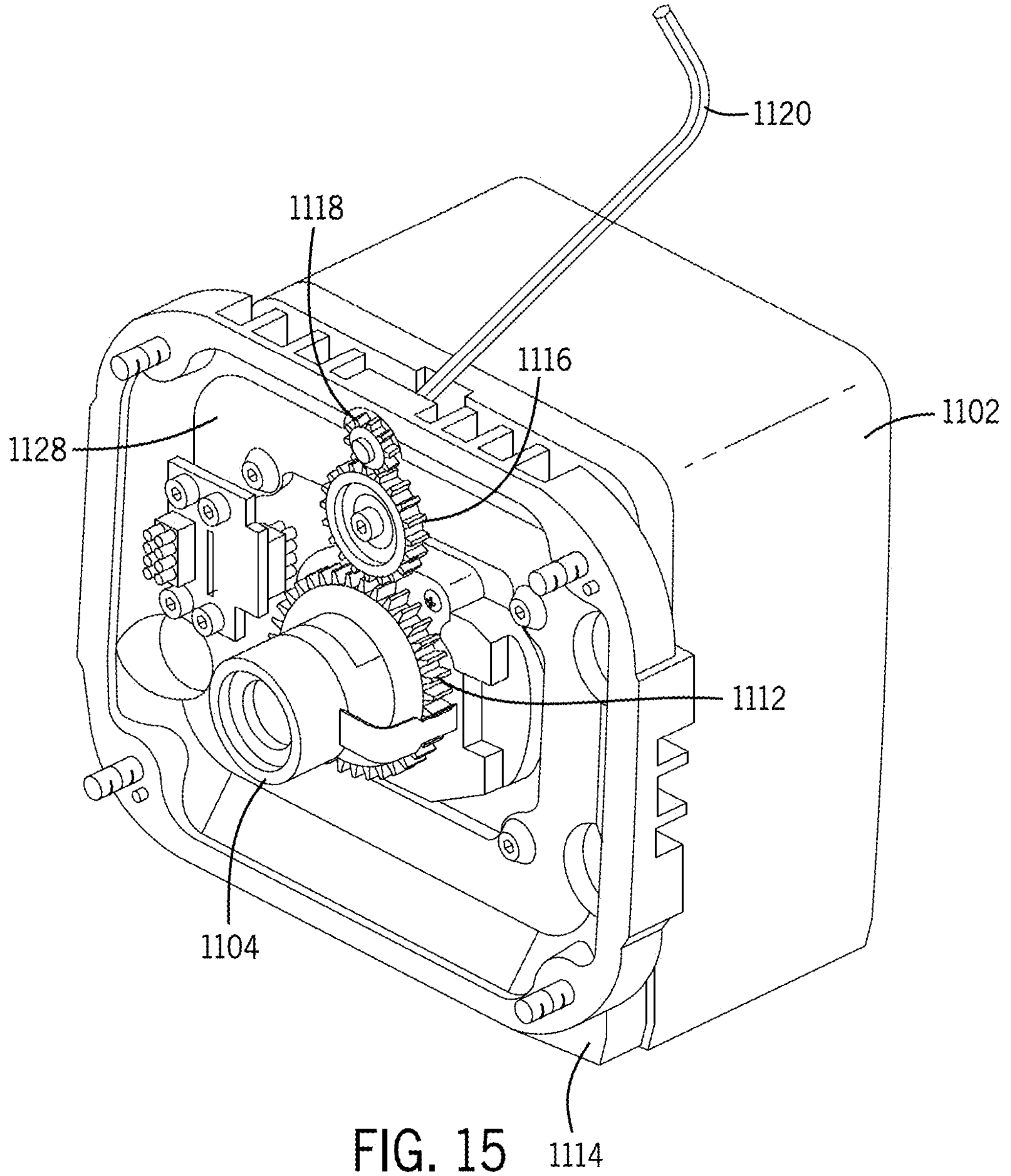
FIG. 15 is perspective view of a back plate of an illumination assembly, a lens assembly and an image sensor assembly in accordance with an embodiment of the technology.

The illumination assembly 1106 is positioned in front of and, when assembled, coupled to the lens assembly 1104, and also partly surrounds the lens assembly 1104 as installed for operation. For example, the illumination assembly 1106 including the back plate 1114 can include an opening in which at least a portion of the lens assembly 1104 can be positioned when assembled (for example, as shown in FIG. 15 described further below). Accordingly, in some embodiments, parts of the lens assembly 1104 can partly protrude into (or even past) the illumination assembly 1106. The lens assembly 1104 and illumination assembly 1106 are shown in an example arrangement in FIG. 11 and it should be understood that different numbers and other arrangements of the lens assembly 1104 and the illumination assembly 1106 may be used in other embodiments. In some embodiments, the illumination assembly 1106 can include a plurality of multispectral light assemblies 1122 such as, for example, multispectral light assembly 100 and multispectral light assemblies 216, 218, 220 described above with respect to FIG. 1 and FIG. 2. The plurality of multispectral light assemblies 1122 are shown in an example arrangement in the illumination assembly 1106 in FIG. 11 and it should be understood that different numbers and other arrangements of multispectral light assemblies may be used in the illumination assembly 1106 in other embodiments. The plurality of multispectral light assemblies 1122 in the illumination assembly 1106 may be used to generate light in multiple wavelengths that may be projected onto an object (not shown) to, for example, acquire an image of the object or an image of an ID on the object. In some embodiments, the plurality of multispectral light assemblies 1122 are positioned symmetrically around the one or more lenses of the lens assembly 1104.

Each multispectral light assembly 1122 in the illumination assembly 1106 may include the same type of multispectral light source or the plurality of multispectral light assemblies 1122 may include different types or a combination of types of multispectral light sources. In some embodiments, the multispectral light source can include a plurality of color LED dies that generate light in multiple wavelengths. In some embodiments, the plurality of color LED dies in the multispectral light source can be provided in a single package. In some embodiments, the multispectral light source may be, for example, an RGB LED, an RGBW LED, an RGB(IR) LED, an RGBY LED, an IR and Red LED, a White and Red LED, or other RGB or multi-wavelength LED type In some embodiments, the illumination assembly 1106 can include a distance senor 1124 (e.g., a time of flight (TOF) sensor), one or more optical filters (not shown), and an indicator 1126 of the projected field of view (FOV) center. As discussed above, the multispectral light assemblies 1122 may be activated in a light banking configuration, including as described above with respect to FIG. 5. A modular front cover 1108 (e.g., clear, diffusing or cross-polarized) can be positioned in front of the illumination assembly 1106. In FIG. 11, an example of three modular front covers 1108 are shown and one of the front covers 1108 may be chosen and positioned in front of the illumination assembly 1106.

In some embodiments, a removable passive light accessory 1110 can be positioned in front of the selected front cover 1108 and the illumination assembly 1106. For example, the passive light assembly 1110 can be a diffused light assembly 900 such as described above with respect to FIG. 9 which can be used to enable the vision system assembly 1100 to convert the illumination light to diffuse light provided at shorter distances. Known mechanical attachment mechanisms may be used to removably attach the passive light accessory 1110. The vision system assembly 1100 may also include other elements that are not shown in FIG. 11 for clarity. For example, the vision system assembly 1100 may include processing components (e.g., a processor 202 shown in FIG. 2) that perform various vision system tasks such as ID code finding and decoding, inspection, etc.

Figure 12:
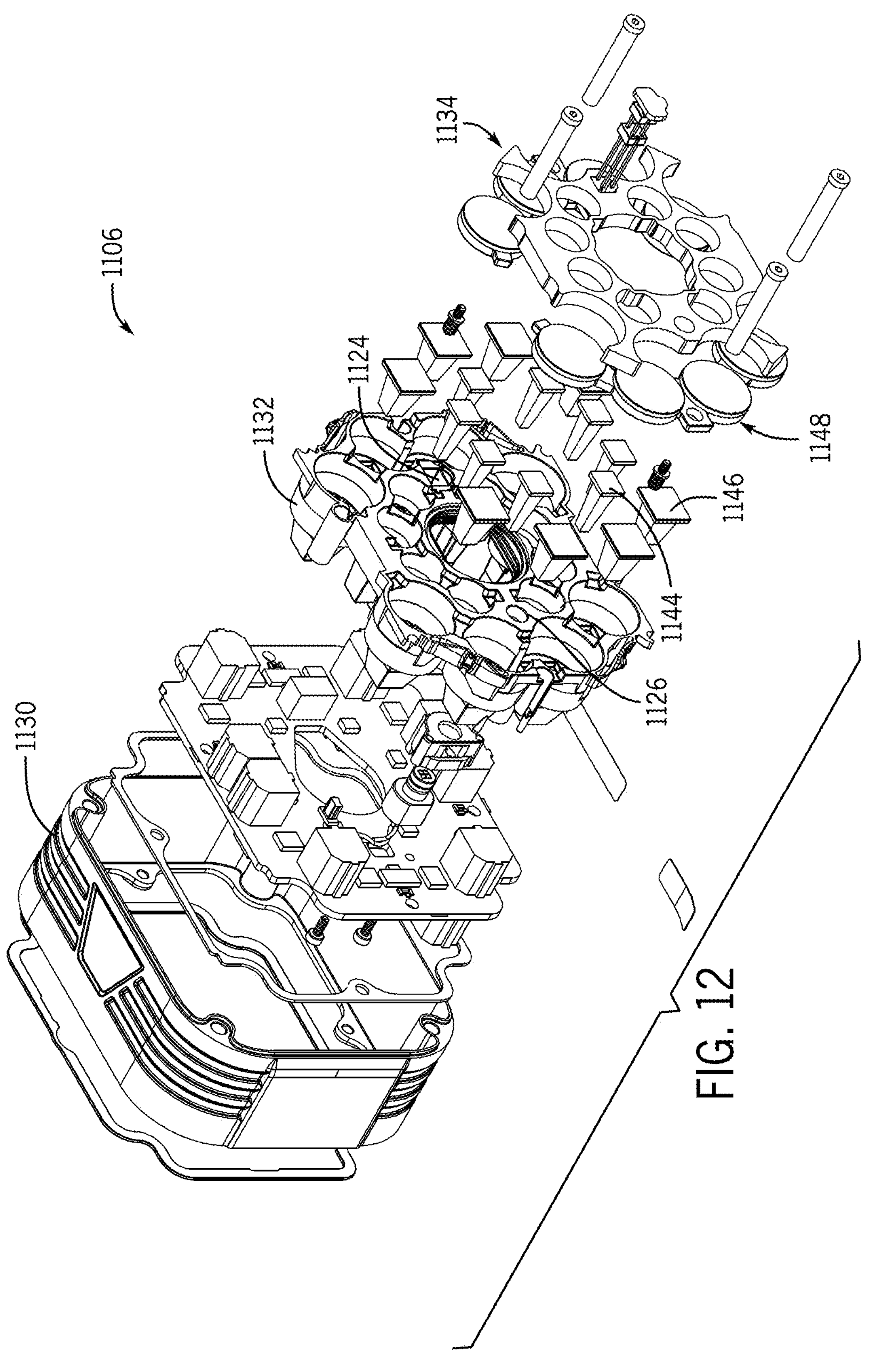
FIG. 12 is an exploded view of an example illumination assembly of the vision system assembly of FIG. 11 in accordance with an embodiment of the technology.

FIG. 12 is an exploded view of an example illumination assembly of the vision system assembly of FIG. 11 in accordance with an embodiment of the technology. The exemplary illumination assembly 1106 can include a housing 1130, a support structure 1132, and a front plate 1134. The support structure 1132 can be configured to support the plurality of multispectral light assemblies (e.g., multispectral light assemblies 1122 shown in FIG. 11). In some embodiments, a multispectral light assembly supported by the support structure 1132 can include a multispectral light source (not shown), a light pipe 1144, a diffuse surface 1146 and a projection lens 1148. For example, each multispectral light assembly may be a multispectral light assembly 100 described above with respect to FIG. 1. The front plate 1134 may include openings configured to receive the projections lens 1147 of each multispectral light assembly supported by the support structure 1132. The plurality of multispectral light assemblies are shown in an example arrangement in the illumination assembly 1106 in FIG. 12 and it should be understood that different numbers and other arrangements of multispectral light assemblies may be used in the illumination assembly 1106 in other embodiments. In some embodiments, the support structure 1132 may also be configured to support a distance sensor 1124 and an indicator device 1126 configured to provide an indication of a projected FOV center.

As discussed above, in some embodiments, one or more illumination sensors (e.g., illumination sensor 222 shown in FIG. 2) may be integrated into the illumination assembly 1106 and located proximate to the multispectral light assemblies, for example, located proximate to or near the multispectral light sources (e.g., LEDs) of the multispectral light assemblies. In some embodiments, a plurality of illumination sensors may be located proximate to or near the projection lenses of the multispectral light assemblies. The illumination sensor(s) and a processor of the vision system may be used to implement a feedback loop that may be used to control the amount of light of the different color channels projected by the illumination assembly 1106 and thereby improve image acquisition, including as discussed above with respect to FIGS. 1 through 8.

Figure 13:
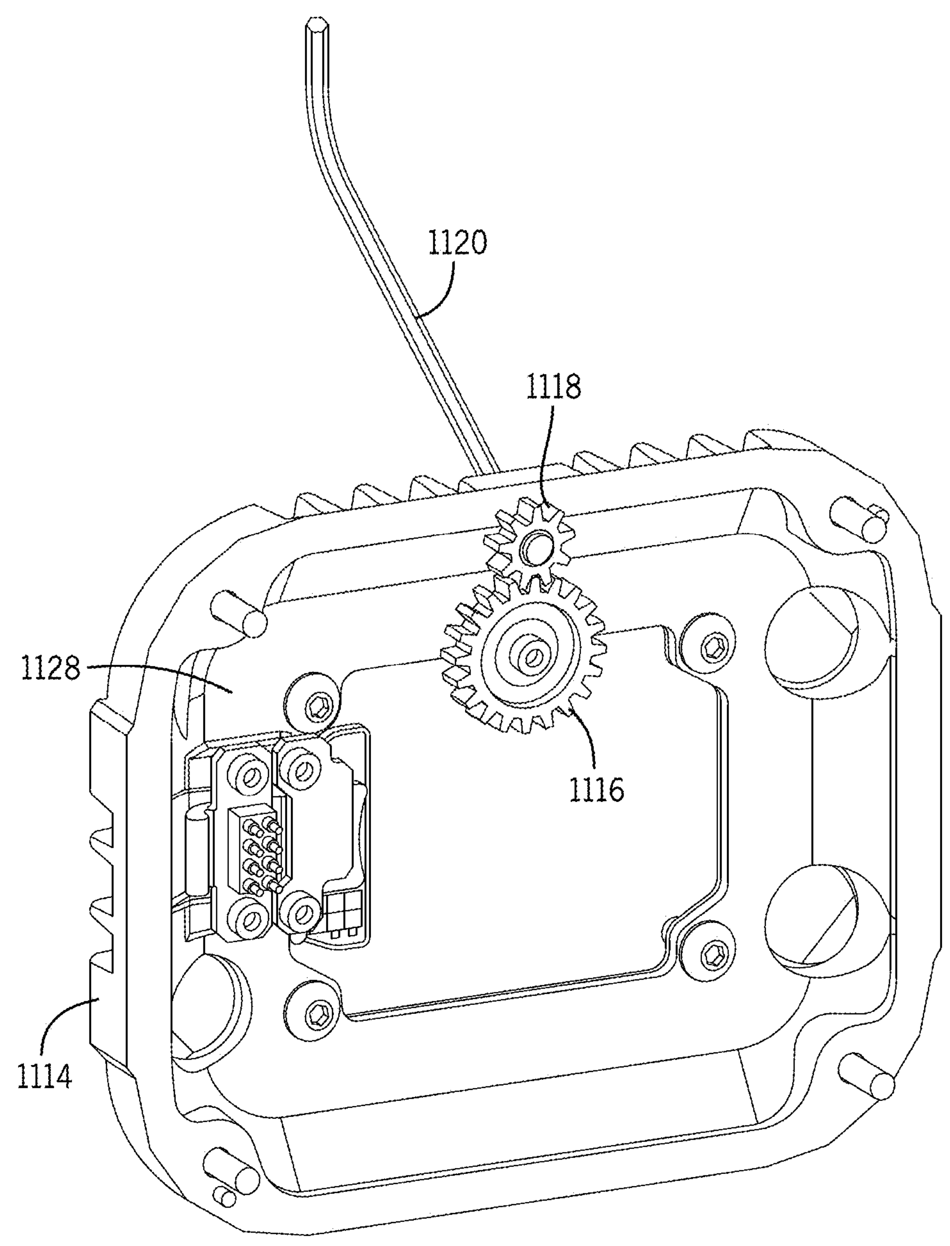
FIG. 13 is a perspective view of an inner surface of a back plate of an illumination assembly in accordance with an embodiment of the technology.
Figure 14:
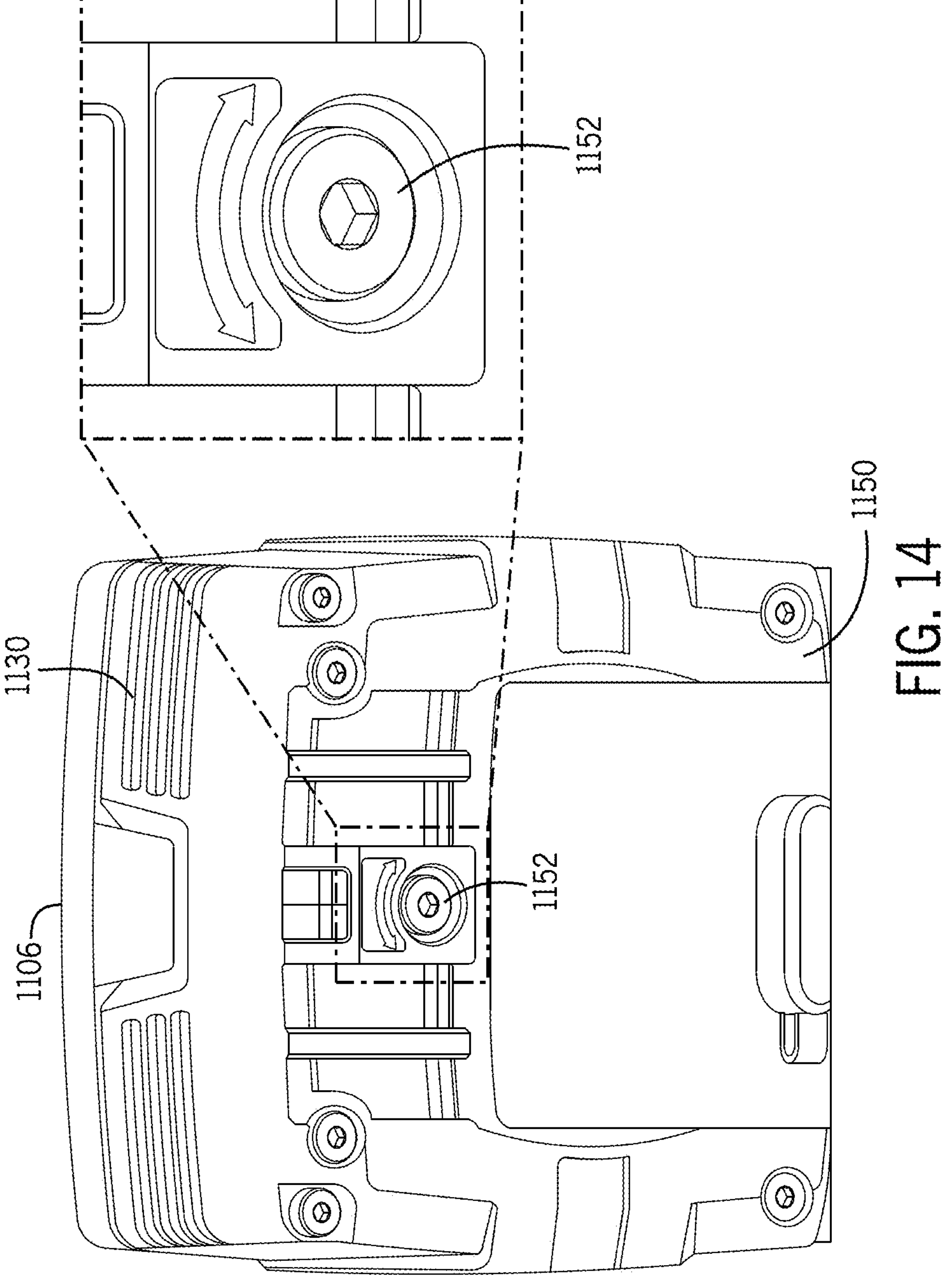
FIG. 14 is a rear view of an illumination assembly including an outer surface of a back plate of the illumination assembly in accordance with an embodiment of the technology.

As mentioned above, in some embodiments, the vision system assembly 1100 may include mechanical parts (e.g., a gear mechanism) that can be used to manually adjust the focus of the lens assembly 1104 by moving the lens assembly 1104 towards or away from the image sensor assembly 1102 to change the focal distance of the system 1100. FIGS. 13-15 illustrate an example gear mechanism for manually adjusting the focus of a lens assembly. FIG. 13 is a perspective view of an inner surface of a back plate of an illumination assembly in accordance with an embodiment of the technology. In FIG. 13, a portion of an exemplary gear mechanism located on the back plate 1114 of the illumination assembly 1106 is shown.

As discussed above, the gear mechanism may include a first gear 1112 (shown in FIG. 15) on a lens assembly 1104, a second gear 1116 positioned on the inside surface 1128 of the back plate 1114 of the illumination assembly 1106, and a third gear 1118 positioned on the inside surface 1128 of the back plate 1114 of the illumination assembly 1106. In some embodiments, a focal adjustment tool 1120 (e.g., an Allen wrench) may be used by an operator to manually drive the third gear 1118, to thereby drive the second gear 1116, which in turn can drive the first gear 1112 (shown in FIG. 15) on the lens assembly to move the lens assembly 1104 (e.g., to move one or more glass lenses within the lens assembly 1104).

FIG. 14 is a rear view of an illumination assembly including an outer surface of a back plate of the illumination assembly in accordance with an embodiment of the technology. In some embodiments, an outer surface 1150 of the back plate 1114 (or other component) of the illumination assembly 1106 can include an opening 1152 configured to receive the focus adjustment tool 1120 (shown in FIGS. 13 and 15). For example, the opening may be configured to receive an Allen wrench (or Hex key).

FIG. 15 is perspective view of a back plate of an illumination assembly, a lens assembly and an image sensor assembly in accordance with an embodiment of the technology. In FIG. 15, a back plate 114 of the illumination assembly 1106 is shown attached to the image sensor assembly 1102. In the illustrated embodiment, the lens assembly 1104 is positioned within the back plate 1114 (e.g., in an opening in the back plate 1114 as shown in FIGS. 11 and 13) of the illumination assembly 1106 so that the first gear 1112 on the lens assembly 1104 is movably engaged with the second gear 1116 positioned on the inner surface 1128 of the back plate 1114 of the illumination assembly 1106. The third gear 118 positioned on the inner surface 1128 of the back plate 1115 is moveably engaged with the second gear 1116. In some embodiments, an operator can position the focus adjustment tool 1120 in the opening 1152 (shown in FIG. 14) of the outer surface 1150 of the back plate and rotate the focus adjustment tool 1120 to cause the third gear 1118 to rotate. Rotation of the third gear 1118 may then cause rotation of the second gear 1116 which in turn can cause rotation of the first gear 1112 on the lens assembly 1104 to move the lens assembly 1104 or one or more glass lenses within the lens assembly 1104.

Figure 16A:
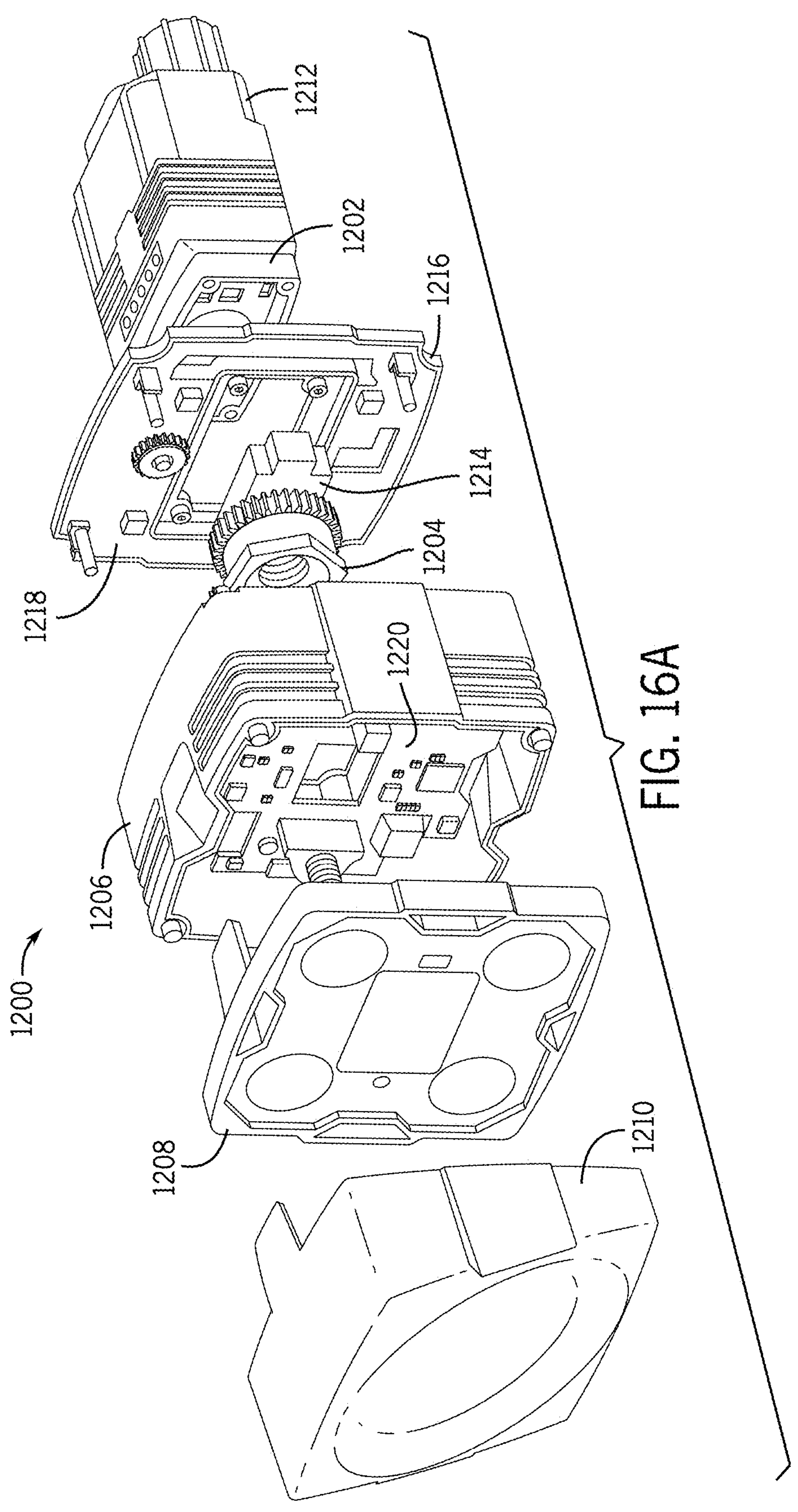
FIG. 16A is an exploded perspective view of a vision system assembly including a plurality of multispectral light assemblies in accordance with an embodiment of the technology.

FIG. 16A is an exploded perspective view of a vision system assembly including a plurality of multispectral light assemblies in accordance with an embodiment of the technology. The vision system assembly can be used to acquire an image of an object (not shown) or an ID on the object. In the illustrated vision system assembly 1200 of FIG. 12, a lens assembly 1204 is positioned in front of and, when assembled, coupled to an image sensor assembly 1102. The image sensor assembly 1202 can include an image sensor that can be configured to detect different wavelengths of light. In some embodiments, the image sensor of the image sensor assembly 1202 can be a monochrome sensor (e.g., black and white) or a color sensor. In some embodiments, the image sensor of the image sensor assembly 1202 can have a size between 2-16 mega-pixels. As discussed above, the lens assembly 1204 may be project an images light onto an area of the image sensor of the image sensor assembly 1202 and, correspondingly, define a FOV for imaging with the image sensor of the image sensor assembly 1202.

In some embodiments, the lens assembly 1204 can include one or more lenses such as, for example, a high speed liquid lens to allow for rapid and automated adjustment of focus for images at different working distances. In other embodiments, the lens assembly 1204 can include one or more glass lenes.

In some embodiments, the vision system assembly 1200 may include mechanical parts (e.g., a gear mechanism) that can be used to manually adjust the focus of the lens assembly 1204 by moving the lens assembly 1204 towards or away from the image sensor assembly 1202 to change the focal distance of the system 1200. For example, a gear mechanism as described above with respect to FIGS. 13-15 can be included in the vision system assembly 1200, for example, the lens assembly 1204 and an inner surface 1218 of a back plate 1216 of the illumination assembly 1206 may include a plurality of gears that can be utilized to manually adjust the position of one or more lenses of the lens assembly 1204. As discussed above with respect to FIGS. 13-15, in some embodiments, a focal adjustment tool (e.g., an Allen wrench) may be used by an operator to manually drive one or more gears on the inner surface 1218 of the back plate 1216 which in turn can drive a gear 1214 on the lens assembly 1204 to move the lens assembly 1204 or one or more glass lenses within the lens assembly 1204. In some embodiments, the one or more glass lenses may be provided with motorized mechanical parts (e.g., gear, motor and thread assembly) that are used to move a one or more lenses toward or away from the image sensor assembly 1202 to change the focal distance of the system 1200

The illumination assembly 1206 is positioned in front of and, when assembled, coupled to the lens assembly 1204 and also partly surrounds the lens assembly 1204 as installed for operation. For example, the illumination assembly 1206 including the back plate 1216 can include an opening in which at least a portion of the lens assembly 1204 can be positioned when assembled. Accordingly, in some embodiments, parts of the lens assembly 1204 can partly protrude into (or even past) the illumination assembly 1206. The lens assembly 1204 and illumination assembly 1206 are shown in an example arrangement in FIG. 12 and it should be understood that different numbers and other arrangements of the lens assembly 1204 and the illumination assembly 1206 may be used in other embodiments. In some embodiments, the illumination assembly 1206 can include a plurality of multispectral light assemblies 1234 (shown in FIG. 17) configured, for example, similarly to multispectral light assembly 100 and multispectral light assemblies 216, 218, 220 described above with respect to FIG. 1 and FIG. 2. The plurality of multispectral light assemblies in the illumination assembly 1206 may be used to generate light in multiple wavelengths that may be projected onto an object (not shown) to, for example, acquire an image of the object or an image of an ID on the object. In some embodiments, the plurality of multispectral light assemblies 1234 are positioned symmetrically around the one or more lenses of the lens assembly 1204. Each multispectral light assembly in the illumination assembly 1206 may include the same type of multispectral light source or the plurality of multispectral light assemblies may include different types or a combination of types of multispectral light sources. In some embodiments, the multispectral light source can include a plurality of color LED dies that generate light in multiple wavelengths. In some embodiments, the plurality of color LED dies in the multispectral light source can be provided in a single package. In some embodiments, the multispectral light source may be, for example, an RGB LED, an RGBW LED, an RGB(IR) LED, an RGBY LED, an IR and Red LED, a White and Red LED, or other RGB or multi-wavelength LED type In some embodiments, the illumination assembly 1206 can include a distance senor 1220 (e.g., a time of flight (TOF) sensor) and one or more optical filters (not shown). As discussed above, the multispectral light assemblies may be activated in a light banking configuration as described above with respect to FIG. 5.

In some embodiments, a front cover 1208 (e.g., clear, diffuse, or cross-polarized) can be positioned in front of the illumination assembly 1206. In some embodiments, the front cover 1208 can be a modular front cove. In some embodiments, the front cover 1208 may also include one or more bandpass filters (not shown).

In some embodiments, a removable passive light accessory 1210 can be positioned in front of the front cover 1208 and the illumination assembly 1206. For example, the passive light assembly 1210 can be a diffused light assembly 900 such as described above with respect to FIG. 9 which can be used to enable the vision system assembly 1200 to convert the illumination light to diffuse light provided at shorter distances. Known mechanical attachment mechanisms may be used to removably attach the passive light accessory 1210. The vision system assembly 1200 may also include other elements that are not shown in FIG. 16A for clarity. For example, the vision system assembly 1200 may include processing components (e.g., a processor 202 shown in FIG. 2) that perform various vision system tasks such as ID code finding and decoding, inspection, etc.

Figure 16B:
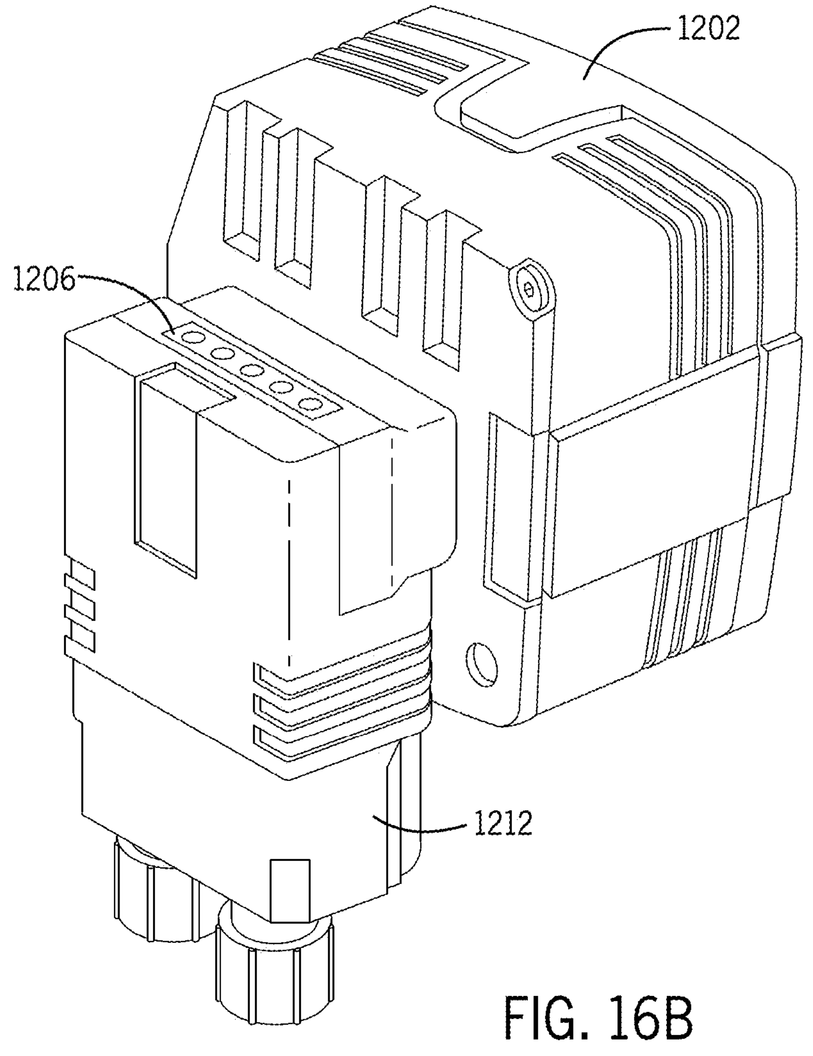
FIG. 16B is a perspective view of the example right angle adapter shown in FIG. 16A in a second position in accordance with an embodiment of the technology.

In other embodiments, an adapter 1212 (e.g., a right angle adapter as shown in FIG. 16B) may connected to the image sensor assembly 1202 and be used to direct cables of the vision system assembly 1200. In FIG. 16A, the adapter 1212 is shown in a first position. In some embodiments, the adapter 1212 may be configured to have a plurality of positions which can be used to redirect the cables of the vision system assembly 1200. FIG. 16B is a perspective view of the example right angle adapter shown in FIG. 16A in a second position in accordance with an embodiment of the technology. In FIG. 16B, the adapter 1212 is coupled to the image sensor assembly 1202 and is in a second position orthogonal to the first position shown in FIG. 16A.

Figure 17:
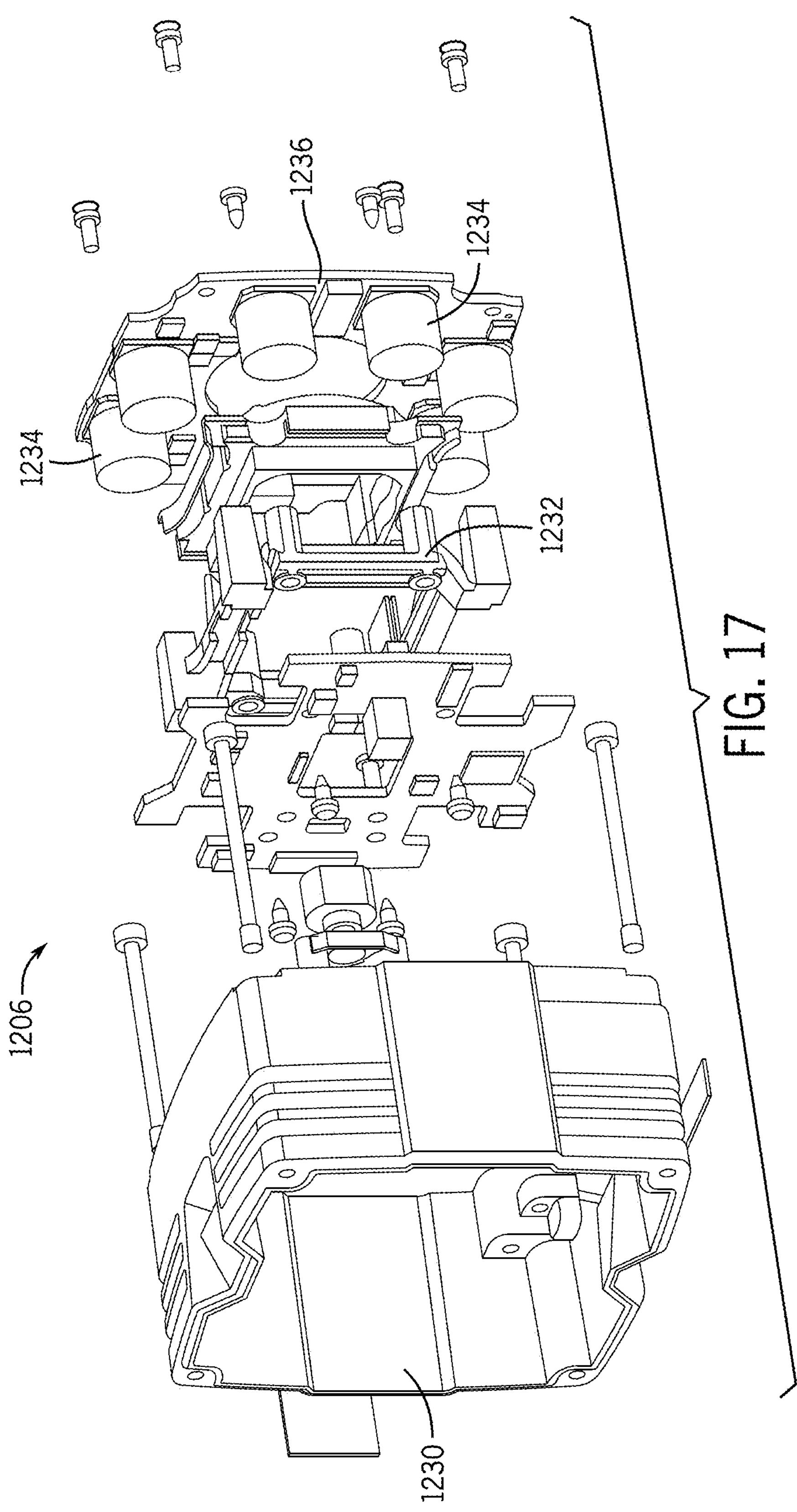
FIG. 17 is an exploded view of an example illumination assembly of the vision system assembly of FIG. 16A in accordance with an embodiment of the technology.

FIG. 17 is an exploded view of an example illumination assembly of the vision system assembly of FIG. 16A in accordance with an embodiment of the technology. The exemplary illumination assembly 1206 can include a housing 1230, a support structure 1232, and a front plate 1234. The support structure 1232 can be configured to support the plurality of multispectral light assemblies 1234. In some embodiments, the multispectral light assemblies 1234 supported by the support structure 1232 can include a multispectral light source, a light pipe, a diffuse surface and a projection lens. For example, each multispectral light assembly 1234 may be a multispectral light assembly 100 as described above with respect to FIG. 1. The front plate 1234 may include openings configured to receive the projections lens of each multispectral light assembly 1234 supported by the support structure 1232. The plurality of multispectral light assemblies 1234 are shown in an example arrangement in the illumination assembly 1206 in FIG. 17 and it should be understood that different numbers and other arrangements of multispectral light assemblies may be used in the illumination assembly 1206 in other embodiments. In some embodiments, the support structure 1232 may also be configured to support a distance sensor.

As discussed above, in some embodiments, one or more illumination sensors (e.g., illumination sensor 222 shown in FIG. 2) may be integrated into the illumination assembly 1206 and located proximate to the multispectral light assemblies, for example, located proximate to or near the multispectral light sources (e.g., LEDs) of the multispectral light assemblies. In some embodiments, a plurality of illumination sensors may be located proximate to or near the projection lenses of the multispectral light assemblies. The illumination sensor(s) and a processor of the vision system may be used to implement a feedback loop that may be used to control the amount of light of the different color channels projected by the illumination assembly 1206 and thereby improve image acquisition, including as generally discussed above.

Figure 18:
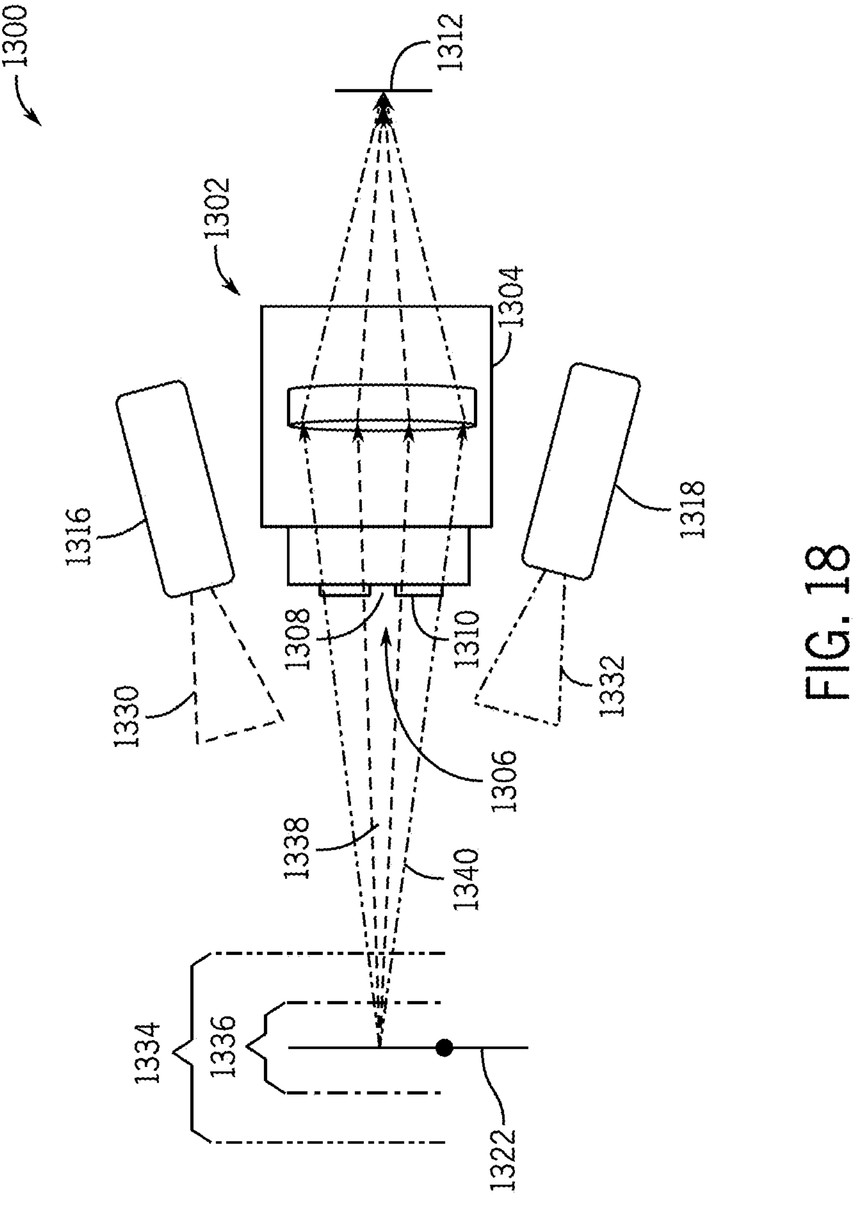
FIG. 18 is a schematic diagram of an illumination apparatus with multispectral light assemblies and an optics assembly with a dual aperture in accordance with an embodiment of the technology.

FIG. 18 is a schematic diagram of an illumination apparatus with multispectral light sources and an optics assembly with a dual aperture, included in a vision system 1300 in accordance with an embodiment of the technology. In some embodiments, multispectral light sources may be utilized in a vision system that includes an optics assembly 1302 with a multiple aperture assembly that can include different regions that can be used with corresponding light sources to acquire images with different DOFs. The vision system 1300 is an example of a particular implementation of a vision system, however, other configurations are also possible. In FIG. 18, the multiple aperture assembly is a dual aperture assembly, however, in other embodiments, additional apertures may be provided.

To acquire an image using an inner region 1308 (small aperture) of the dual aperture assembly 1306 and a larger DOF 1334, a first light source 1316 projects a light beam 1330 having a particular wavelength (or range of wavelengths) or polarization on a target 1322 (e.g., a barcode). The reflected light 1338 of the first light beam passes through the inner region 1308 of the dual aperture assembly 1306 and is blocked by the outer region 1310. The reflected light 1338 is then directed to the image sensor 1312 by one or more lenses of the lens arrangement 1304. To acquire an image using the outer region 1310 (large aperture) of the dual aperture assembly 1306 and a smaller DOF 1336, a second light source 1318 projects a light beam 1332 having a particular wavelength (or range of wavelengths) or polarization on the target 1322 (e.g., a barcode). The reflected light 1340 of the second light beam passes through the entire diameter of the dual aperture assembly 1306 (i.e., a combined diameter of the inner region 1308 and the outer region 1310) and is directed to the image sensor 1312 by one or more lenses of the lens arrangement 1304. In the illustrated embodiment, the first region 1308 and the second region 1310 of the dual aperture assembly 1306 have the same focal point for the first light beam 1330 and the second light beam 1332.

The image sensor 1312 can include rows and columns of photosensitive sites (pixels) that form a pixel array. When the reflected light (1338 or 340) is projected by the lens arrangement 1304 onto the image sensor 1312, each pixel produces a signal which is proportional to the light incident on that pixel. In some embodiments, the sensor 1312 is a monochrome sensor. The dual aperture assembly can be used to, for example, acquire individual images at different times using the different regions and the corresponding light source. Accordingly, depending on the wavelength or polarization used to illuminate the target 1322, the reader will have a different aperture value and, thus, a different DOF and exposure time for acquiring an image.

In some embodiments, the light sources 1316 and 1318 used to project the first illumination light 1330 and the second illumination light 1332 can each include an LED or laser diode to provide illumination light of a particular type (wavelength or polarization). In some embodiments, a multispectral light source may be used to provide both the first illumination light 1330 and the second illumination light 1332. For example, the multispectral light source may be part of a multispectral light assembly 216, 218, 220 as described above with respect to FIG. 2 In some embodiment, the multispectral light source can include various color LED dies in a single package. For example, the multispectral light source may be an RGB LED, an RGBW LED, an RGB(IR) LED, an RGBY LED, or other RGB or multi-wavelength LED type.

A vision system that includes and utilizes at least one multispectral light source (e.g., a multispectral light assembly) can be advantageous for a number of different imaging applications. For example, in some embodiments, using multiple wavelengths of light (i.e., multiple colors) or combinations of wavelengths can advantageously enable the ability to distinguish between featured to be analyzed on the same image. In such embodiments, the vision system assembly may include a clear front cover in combination with the plurality of wavelengths that can be generated by each multispectral light source (e.g., RGBW LEDs). In some embodiments, a vision system with multispectral light sources may be advantageous to obtaining an image of an object or target that has oil of other type of transparent surface. Different wavelengths of light (and mixing colors) can be used to create different interactions with an object (e.g., a surface of an object) and make a transparent surface, such as, for example, oil, easier to detect. In such embodiments, the vision system assembly may include a clear front cover in combination with the plurality of wavelengths that can be generated by each multispectral light source (e.g., RGBW LEDs). In addition, for such embodiments, the vision system may utilize a timing configuration for a single exposure as described above with respect to FIG. 8

In some embodiments, a vision system with multispectral light sources (e.g., a multispectral light assembly) may be advantageous for optical character recognition (OCR) applications. For example, a vision system configured for OCR may utilize polarized light and the camera of the vision system may view a scene with another polarizer filter that is tilted 90 degrees with respect to the camera. The color available from the multispectral light sources or assemblies can be key to improving contrast and/or brightness. In OCR applications, the vision system assembly may include a polarized front cover and the vision system may utilize a timing configuration for a single exposure as described above with respect to FIG. 8.

In some embodiments, a vision system with multispectral light sources (e.g., a multispectral light assembly) may be advantageous for diffused light applications such as, for example, imaging parts with a cylindrical or non-flat shape. Cylindrical parts imaged for ID or OCR applications can be challenging because of reflections and texture. Diffuse light with different color (or wavelength) possibilities can be advantageously used to expand the performance of a vision system. For example, a diffused light assembly such as described above with respect to FIG. 9 can be combined with of a vision system illumination assembly including multispectral light assemblies and the vision system may utilize a timing configuration for a single exposure as described above with respect to FIG. 8 In some embodiments, vision system with multispectral light sources (e.g., a multispectral light assembly) may be advantageous for application to identify defects on fabrics. In such embodiments, a vision system assembly may include a combination of multispectral light sources (e.g., multispectral light assemblies), and one or more of polarized light, a clear front cover, and/or diffuse light (e.g., using a diffused light assembly shown in FIG. 9).

In some embodiments, a vision system with multispectral light sources (e.g., a multispectral light assembly) may be advantageous for security applications, for example to improve image quality for identifying tiny features on an object or target or detecting security features on paper currency, watermarks, etc. Such applications may utilize multispectral light sources that can provide infrared (IR) light). In such embodiments, a vision system assembly may include a combination of multispectral light sources (e.g., multispectral light assemblies), and a clear front cover or diffuse light (e.g., using a diffused light assembly shown in FIG. 9). In some embodiments, a vision system with multispectral light sources (e.g., a multispectral light assembly) may be advantageous for identifying three-dimensional (3D) structures, for example, detecting gap interfaces between structures. In such embodiments, a vision system assembly may include a combination of multispectral light sources (e.g., multispectral light assemblies) and diffuse light (e.g., using a diffused light assembly shown in FIG. 9). For 3D structures, using different colors can reveal more feedback in terms of brightness as a consequence of material properties.

In some embodiments, a vision system with multispectral light sources (e.g., a multispectral light assembly) may be advantageous for 3D printing and scanning applications. In such embodiments, the vision system may utilize a timing configuration for a single exposure as described above with respect to FIG. 8 to, for example, produce color mixing capabilities. In addition, for 3D printing and scanning application, the vision system assembly may include a diffused light assembly such as, for example, the diffused light assembly shown in FIG. 9. In some embodiments, a vision system with multispectral light sources (e.g., a multispectral light assembly) may be advantageous for medical and life science applications such as, for example, skin cancer recognition, detection and monitoring of jaundice, bilirubin level detection, etc. In such embodiments, the vision system can utilize a timing configuration for a single exposure as described above with respect to FIG. 8 to, for example, produce color mixing capabilities. In addition, for 3D printing and scanning application, the vision system assembly may include a diffused light assembly such as, for example, the diffused light assembly shown in FIG. 9. In some embodiments, a vision system with multispectral light sources (e.g., a multispectral light assembly) may be advantageous for agricultural applications, for example, quality inspection and production control. In some agricultural applications, the vision system assembly may include a clear front cover.

In some embodiments, various applications of a vision system mentioned above such as, for example, detection of defects on fabrics, imaging of 3D structures, medical and life science applications, agricultural applications, etc. may utilize machine learning (e.g., deep learning) techniques for the analysis of images. It may be advantageous to use of a vision system with multispectral light sources (e.g., a multispectral light assembly) to acquire images used for training of a neural network and to acquire images to be analyzed by a neural network because of, for example, better image quality.

The foregoing has been a detailed description of illustrative embodiments of the technology. Various modifications and additions can be made without departing from the spirit and scope of this disclosure. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present disclosure, what has been described herein is merely illustrative of the application of the principles of the present disclosure. Also, as used herein various directional and orientation terms such as "vertical", "horizontal", "up", "down", "bottom", "top", "side", "front", "rear", "left", "right", and the like are used only as relative conventions and not as absolute orientations with respect to a fixed coordinate system, such as gravity. Accordingly, the description is meant to be taken only by way of example, and not to otherwise limit the scope of this disclosure.

In some embodiments, aspects of the technology, including computerized implementations of methods according to the technology, can be implemented as a system, method, apparatus, or article of manufacture using standard programming or engineering techniques to produce software, firmware, hardware, or any combination thereof to control a processor device (e.g., a serial or parallel general purpose or specialized processor chip, a single- or multi-core chip, a microprocessor, a field programmable gate array, any variety of combinations of a control unit, arithmetic logic unit, and processor register, and so on), a computer (e.g., a processor device operatively coupled to a memory), or another electronically operated controller to implement aspects detailed herein. Accordingly, for example, embodiments of the technology can be implemented as a set of instructions, tangibly embodied on a non-transitory computer-readable media, such that a processor device can implement the instructions based upon reading the instructions from the computer-readable media. Some embodiments of the technology can include (or utilize) a control device such as an automation device, a special purpose or general purpose computer including various computer hardware, software, firmware, and so on, consistent with the discussion below. As specific examples, a control device can include a processor, a microcontroller, a field-programmable gate array, a programmable logic controller, logic gates etc., and other typical components that are known in the art for implementation of appropriate functionality (e.g., memory, communication systems, power sources, user interfaces and other inputs, etc.).

The term "article of manufacture" as used herein is intended to encompass a computer program accessible from any computer-readable device, carrier (e.g., non-transitory signals), or media (e.g., non-transitory media). For example, computer-readable media can include but are not limited to magnetic storage devices (e.g., hard disk, floppy disk, magnetic strips, and so on), optical disks (e.g., compact disk (CD), digital versatile disk (DVD), and so on), smart cards, and flash memory devices (e.g., card, stick, and so on). Additionally, it should be appreciated that a carrier wave can be employed to carry computer-readable electronic data such as those used in transmitting and receiving electronic mail or in accessing a network such as the Internet or a local area network (LAN). Those skilled in the art will recognize that many modifications may be made to these configurations without departing from the scope or spirit of the claimed subject matter.

Certain operations of methods according to the technology, or of systems executing those methods, may be represented schematically in the FIGS., or otherwise discussed herein. Unless otherwise specified or limited, representation in the FIGS. of particular operations in particular spatial order may not necessarily require those operations to be executed in a particular sequence corresponding to the particular spatial order. Correspondingly, certain operations represented in the FIGS., or otherwise disclosed herein, can be executed in different orders than are expressly illustrated or described, as appropriate for particular embodiments of the technology. Further, in some embodiments, certain operations can be executed in parallel, including by dedicated parallel processing devices, or separate computing devices configured to interoperate as part of a large system.

As used herein in the context of computer implementation, unless otherwise specified or limited, the terms "component," "system," "module," and the like are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

The invention claimed is:

1. A machine vision system comprising:
- an image sensor assembly including an image sensor;
- a lens assembly positioned in front of the image sensor assembly;
- an illumination assembly disposed around a portion of the lens assembly, the illumination assembly including:
  - a plurality of multispectral light assemblies, wherein each multispectral light assembly of the plurality of multispectral light assemblies includes:
    - a multispectral light source having a plurality of color LED dies configured to generate at least two different wavelengths of light;
    - a light pipe positioned in front of the multispectral light source, the light pipe having an exit surface;
    - a diffusive surface on the exit surface of the light pipe; and
    - a projection lens positioned in front of the diffusive surface; and
- a removable front cover positioned in front of the illumination assembly including the projection lens of each multispectral light assembly; and
- a passive light accessory removably attached to the machine vision system and positioned in front of the removable front cover and the illumination assembly.

2. The machine vision system according to claim 1, wherein the passive light accessory is a diffused light assembly configured to convert light transmitted from the illumination assembly to a diffuse light.

3. The machine vision system according to claim 1, wherein a portion of the front cover is configured to diffuse light from the illumination assembly.

4. The machine visions system according to claim 1, wherein a portion of the front cover is configured to provide cross-polarization.

5. The machine visions system according to claim 1, further comprising:
- an illumination sensor positioned to detect light transmitted from the illumination assembly; and
- a distance sensor.

6. The machine vision system according to claim 5, wherein the distance sensor is a time of flight sensor (TOF).

7. The machine vision system according to claim 1, further comprising a manual focus adjustment mechanism for adjusting the focus of the lens assembly.

8. The machine visions system according to claim 1, further comprising a multiple aperture assembly positioned in front of the lens assembly.

9. A machine vision system comprising:
- an image sensor assembly including an image sensor;
- a lens assembly positioned in front of the image sensor assembly, the lens assembly including a plurality of lenses and a first gear positioned around the lens assembly;
- an illumination assembly disposed around a portion of the lens assembly, the illumination assembly including:
  - a housing including an inside surface, an outer surface and a front plate;
  - a gear mechanism disposed within the illumination assembly housing and positioned directly on the inside surface of the illumination assembly housing and movably engaged with the first gear on the lens assembly;
  - an opening in the outer surface of the illumination assembly housing configured to receive a tool to engage the gear mechanism to manually adjust the focus of the lens assembly;
  - a plurality of openings in the front plate of the illumination assembly housing; and
  - a plurality of multispectral light assemblies, and
- a removable front cover positioned in front of the illumination assembly.

10. The machine vision system according to claim 9, wherein each multispectral light assembly of the plurality of multispectral light assemblies comprises:
- a multispectral light source having a plurality of color LED dies configured to generate at least two different wavelengths of light;
- a light pipe positioned in front of the multispectral light source, the light pipe having an exit surface;
- a diffusive surface on the exit surface of the light pipe; and
- a projection lens positioned in front of the diffusive surface.

11. The machine vision system according to claim 10, wherein each of the plurality of openings of the front plate of the illumination assembly is configured to receive a projection lens of a corresponding one of the plurality of multispectral light assemblies.

12. The machine visions system according to claim 9, further comprising a passive light accessory removably and attached to the machine vision system and positioned in front of the removable front cover.

13. The machine vision system according to claim 9, wherein the gear mechanism includes:
- a second gear positioned directly on the inside surface of the illumination assembly housing and movably engaged with the first gear on the lens assembly; and
- a third gear positioned directly on the inside surface of the illumination assembly housing and movably engaged with the second gear.

14. The machine vision system according to claim 13, wherein rotation of the third gear drives rotation of the second gear and the first gear to cause movement of at least one lens in the lens assembly.

15. The machine vision system according to claim 14, wherein the movement of the at least one lens is towards or away from the image sensor assembly.

16. The machine vision system according to claim 14, wherein the third gear is configured to be rotated by the tool to adjust the focus of the lens assembly.

17. The machine vision system according to claim 9, wherein a portion of the front cover is configured to at least one of (1) diffuse light from the illumination assembly or (2) provide cross polarization.

18. The machine visions system according to claim 9, further comprising:
- an illumination sensor positioned to detect light transmitted from the illumination assembly; and
- a distance sensor.

19. The machine visions system according to claim 9, further comprising a multiple aperture assembly positioned in front of the lens assembly.

* * * * *